(12) United States Patent
Schewel et al.

(10) Patent No.: US 11,419,719 B2
(45) Date of Patent: Aug. 23, 2022

(54) METHODS AND SYSTEMS FOR ASSISTING OR REPAIRING PROSTHETIC CARDIAC VALVES

(71) Applicant: MTEx Cardio AG, Pfaffikon (CH)

(72) Inventors: Jury Schewel, Hamburg (DE);
Karl-Heinz Kuck, Hamburg (DE);
Tom Saul, Moss Beach, CA (US)

(73) Assignee: MTEx Cardio AG, Ptaffikon (CH)

( * ) Notice: Subject to any disclaimer, the term of this patent is extended or adjusted under 35 U.S.C. 154(b) by 0 days.

(21) Appl. No.: 16/529,247

(22) Filed: Aug. 1, 2019

(65) Prior Publication Data

US 2019/0350705 A1 Nov. 21, 2019

Related U.S. Application Data

(63) Continuation of application No. PCT/IB2018/000145, filed on Feb. 5, 2018, and a continuation of application No. PCT/US2018/016811, filed on Feb. 5, 2018.

(60) Provisional application No. 62/570,336, filed on Oct. 10, 2017, provisional application No. 62/455,427, filed on Feb. 6, 2017.

(51) Int. Cl.
*A61F 2/24* (2006.01)

(52) U.S. Cl.
CPC .......... *A61F 2/2427* (2013.01); *A61F 2/2418* (2013.01); *A61F 2/2445* (2013.01); *A61F 2/2454* (2013.01); *A61F 2/2466* (2013.01); *A61F 2/2475* (2013.01); *A61F 2220/0016* (2013.01); *A61F 2220/0075* (2013.01)

(58) Field of Classification Search
CPC .... A61F 2/2442; A61F 2/2445; A61F 2/2454; A61F 2/246; A61F 2/2463
See application file for complete search history.

(56) References Cited

U.S. PATENT DOCUMENTS

| 5,810,882 A | 9/1998 | Bolduc et al. |
| 6,419,695 B1 | 7/2002 | Gabbay |

(Continued)

FOREIGN PATENT DOCUMENTS

| CN | 101068508 A | 11/2007 |
| CN | 103338726 A | 10/2013 |

(Continued)

OTHER PUBLICATIONS

International search report dated Feb. 5, 2015 for PCT/IB2014/002155.

(Continued)

*Primary Examiner* — Leslie Lopez
(74) *Attorney, Agent, or Firm* — Wilson Sonsini Goodrich & Rosati

(57) ABSTRACT

A prosthetic valve coaptation assist device includes an anchor and a single valve assist leaflet. The anchor may be a supporting ring frame, brace or arc structure and will usually be radially self-expandable so that it can expand against surrounding natural or prosthetic tissue. The valve assist leaflet may be made of pericardium or other biological or artificial material and is shaped like the native target valve leaflet. The valve assist leaflet is typically sized larger than the target natural or prosthetic leaflet so that after implantation a significant overlap of the device body occurs.

20 Claims, 27 Drawing Sheets

(56) References Cited

U.S. PATENT DOCUMENTS

| | | |
|---|---|---|
| 6,478,776 B1 | 11/2002 | Rosenman et al. |
| 6,663,633 B1 | 12/2003 | Pierson, III |
| 6,869,444 B2 | 3/2005 | Gabbay |
| 6,986,775 B2 | 1/2006 | Morales et al. |
| 7,160,322 B2 | 1/2007 | Gabbay |
| 7,374,572 B2 | 5/2008 | Gabbay |
| 7,544,198 B2 | 6/2009 | Parodi |
| 7,988,725 B2 | 8/2011 | Gross et al. |
| 8,449,599 B2 | 5/2013 | Chau et al. |
| 8,870,936 B2 | 10/2014 | Rowe |
| 9,445,893 B2 | 9/2016 | Vaturi et al. |
| 9,592,121 B1 | 3/2017 | Khairkhahan |
| 10,166,098 B2 | 1/2019 | Khairkhahan et al. |
| 2001/0021872 A1 | 9/2001 | Bailey et al. |
| 2005/0004668 A1 | 1/2005 | Aklog et al. |
| 2005/0010287 A1 | 1/2005 | Macoviak et al. |
| 2005/0038509 A1 | 2/2005 | Ashe |
| 2005/0107871 A1 | 5/2005 | Realyvasquez et al. |
| 2005/0159810 A1 | 7/2005 | Filsoufi |
| 2005/0235511 A1 | 10/2005 | Tkachyk |
| 2006/0235511 A1 | 10/2006 | Osborne |
| 2006/0293698 A1 | 12/2006 | Douk |
| 2007/0185571 A1 | 8/2007 | Kapadia et al. |
| 2009/0132036 A1 | 5/2009 | Navia |
| 2010/0298929 A1 | 11/2010 | Thornton et al. |
| 2011/0319990 A1 | 12/2011 | Macoviak et al. |
| 2012/0150290 A1 | 6/2012 | Gabbay |
| 2012/0197388 A1 | 8/2012 | Khairkhahan et al. |
| 2013/0023985 A1 | 1/2013 | Khairkhahan et al. |
| 2013/0103140 A1 | 4/2013 | Subramanian et al. |
| 2014/0025163 A1* | 1/2014 | Padala ............... A61F 2/2442 623/2.18 |
| 2014/0067048 A1 | 3/2014 | Chau et al. |
| 2014/0350662 A1 | 11/2014 | Vaturi |
| 2014/0358223 A1 | 12/2014 | Rafiee et al. |
| 2015/0119981 A1 | 4/2015 | Khairkhahan et al. |
| 2015/0119982 A1 | 4/2015 | Quill et al. |
| 2016/0166382 A1 | 6/2016 | Nguyen |
| 2016/0184098 A1 | 6/2016 | Vaturi |
| 2016/0302917 A1 | 10/2016 | Schewel |
| 2017/0112618 A1* | 4/2017 | Li ............... A61F 2/2445 |
| 2019/0201192 A1 | 7/2019 | Kruse et al. |
| 2020/0383776 A1 | 12/2020 | Schewel |

FOREIGN PATENT DOCUMENTS

| | | |
|---|---|---|
| CN | 104582637 A | 4/2015 |
| CN | 105246431 A | 1/2016 |
| CN | 104055600 B | 2/2016 |
| CN | 105451688 A | 3/2016 |
| EP | 2863844 A1 | 4/2015 |
| WO | WO-2014207575 A2 | 12/2014 |
| WO | WO-2014144937 A3 | 4/2015 |
| WO | WO-2015195823 A1 | 12/2015 |
| WO | WO-2016098104 A2 | 6/2016 |
| WO | WO-2018142217 A2 | 8/2018 |

OTHER PUBLICATIONS

Office Action dated Jun. 1, 2017 for U.S. Appl. No. 14/901,468.
U.S. Appl. No. 14/901,468 Office Action dated Mar. 7, 2019.
U.S. Appl. No. 14/901,468 Office Action dated Mar. 8, 2018.
Office action dated Sep. 26, 2018 for U.S. Appl. No. 14/901,468.
Office action dated Nov. 5, 2019 for U.S. Appl. No. 14/901,468.
Office action dated May 13, 2020 for U.S. Appl. No. 14/901,468.
EP18720349.2 Communication pursuant to Rule 164(2)(b) and Article 94(3) EPC dated Feb. 3, 2021.

* cited by examiner

METHODS AND SYSTEMS FOR ASSISTING OR REPAIRING PROSTHETIC CARDIAC VALVES

CROSS-REFERENCE TO RELATED APPLICATIONS

This application is a continuation of PCT Application No. PCT/US18/16811, filed Feb. 5, 2018; which claims priority to U.S. Provisional Patent Application Nos. 62/570,336, filed Oct. 10, 2017; and 62/455,427, filed Feb. 6, 2017, the full disclosures of which are incorporated herein by reference; and this application is also a continuation of PCT Application No. PCT/IB2018/000145, filed Feb. 5, 2018; which claims priority to U.S. Provisional Patent Application Nos. 62/570,336, filed Oct. 10, 2017; and 62/455,427, filed Feb. 6, 2017, the full disclosures of which are incorporated herein by reference.

The subject matter of this application is also related to the subject matter of U.S. patent application Ser. No. 14/901,468, filed Dec. 28, 2015; which is a U.S. national stage entry of PCT Application No. PCT/IB2014/002155, filed Jun. 13, 2014; which claims the benefit of U.S. Provisional Patent Application Nos. 61/956,683, filed on Jun. 14, 2013; 61/963,330, filed on Dec. 2, 2013; and 61/982,307, filed on Apr. 21, 2014; the full disclosures of which are incorporated herein by reference.

BACKGROUND OF THE INVENTION

1. Field of the Invention

The present invention relates generally to medical devices and methods. More particularly, this invention relates to prosthetic devices and methods for improving the function of prolapsing heart and other circulatory valves.

Mitral valve insufficiency, either organic (primary) or functional (secondary), such as but not limited to prolapsed, regurgitation, and dithering (MVI) is a valvular heart disease characterized by the displacement of an abnormally thickened mitral valve leaflet into the left atrium during systole which can result in poor coaptation of the individual valve leaflets and valve leakage against backpressure. There are various types of MVI, broadly classified as classic and non-classic. In its non-classic form, MVI carries a low risk of complications and often can be kept minimal by dietary attention. In severe cases of classic MVI, complications include mitral regurgitation, infective endocarditis, congestive heart failure, and, in rare circumstances, cardiac arrest, usually resulting in sudden death. The aortic valve can also suffer from prolapse, and valves of the venous circulation can suffer from a similar condition which can lead to chronic venous insufficiency resulting from damaged or "incompetent" valves which are characterized by poor coaptation.

It would be desirable to provide apparatus and methods for improving valve function in a patient suffering from any of the conditions identified above and, in particular, for improving coaptation of cardiac vales, including both mitral valves and aortic valves, as well as venous valves. At least some of these objectives will be met by the inventions described below.

2. Background Art

U.S. Pat. Nos. 6,419,695; 6,869,444; and 7,160,322; and U.S. Patent Publication Nos. 2012/0197388 and 2013/0023985 all have disclosure pertinent to the present invention.

SUMMARY OF THE INVENTION

The description of a prosthetic valve device and implantation method is provided. The present invention generally provides medical devices, systems, and methods often used for treatment of mitral valve regurgitation and other valvular diseases including tricuspid regurgitation.

The prosthetic valve device is comprised of a single leaflet sutured to a supporting ring frame, brace or arc structure. The ring frame (referred to henceforth as device ring) is radially self-expandable so that it can expand against the walls of the atrium. The valve device leaflet (referred to henceforth as device body) is made of pericardium or other biological or artificial material and is shaped like the native target valve leaflet. The device body is sized larger than the target leaflet so that after implantation a significant overlap of the device body occurs.

The invention described herein is generally comprised of a percutaneous transcatheter delivery system, a coaptation assisting device and the implantable device body is capable of assuming both a delivery and operational configuration; the delivery configuration being of a small enough size to enable delivery to the implantation site via a percutaneous transcatheter.

The device ring is generally made of metal (e.g., Nitinol), polymer (e.g., polyurethane) or organic substance (e.g., pericardium). At the treatment site the device ring generally is fixed to the annular base of the target valve by anchors which may be part of the device itself or separate from it.

The device body is generally made of synthetic substance (e.g., Dacron or Polyurethane) or organic substance (e.g., pericardium) in some embodiments with an embedded skeleton made of metal, synthetic substance, or organic substance, and in some embodiments with a specially designed inferior ledge to prevent systolic prolapsing of the device body.

The device body is generally placed in atrioventricular direction along the blood flow path like the leaflets of the native valve to move back and forth between an open-valve configuration and a closed-valve configuration.

During implantation the device ring should be positioned closely above the ostium of the target valve from the atrial side (e.g., by a transseptal approach). After insertion of the device, the device body leaflet moves within the blood flow synchronously with the target valve leaflet. In the systole after closing of the target valve, the overlap of the device body will be stopped by the edge of the opposing leaflet of the target valve. Thereby the device overlaps the effective regurgitation area (ERO) and minimizes or eliminates the valve regurgitation.

To close or diminish the gap caused by malcoaptation of the native leaflets the device body will be disposed between the native leaflets, thereby providing a surface to coapt against for at least one of the native leaflets, while effectively replacing the function of the second native leaflet in the area of the valve, which it would occlude during systole.

Among other uses, the coaptation assistance device, device body implants, and methods described herein may be configured for treating functional and/or degenerative mitral valve regurgitation (MR) by creating an artificial coaptation zone within which at least one of the native mitral valve leaflets can seal. The structures and methods herein will largely be tailored to this application, though alternative embodiments might be configured for use in other valves of the heart and/or body, including the tricuspid valve, valves of the peripheral vasculature, the inferior vena cava, or the like.

In a first specific aspect, the present invention comprises a prosthetic valve coaptation assist device including an anchor configured to be attached to a native valve annulus and a single valve assist leaflet attached to the anchor and configured to lie over a superior surface of a first native valve leaflet when the anchor is attached to the native valve annulus. The single valve assist leaflet is sufficiently flexible so that it will move in unison with the first native valve leaflet and will coapt with a second native valve leaflet in response to blood flow through the valve. In this way, valve prolapse can be reduced and leakage minimized.

In some embodiments of the prosthetic valve coaptation assist device, the anchor is configured to self-expand to attach to the native valve annulus. In other embodiments, the anchor may be configured to be sutured to the native valve annulus. For both self-expanding and sutured anchors, the anchor may be further configured to either fully or partially circumscribe the valve annulus. Anchors which partially circumscribe the valve annulus will frequently have barbs or other tissue-penetrating element which help hold the anchor in place, although barbs may be included on fully circumscribing anchors as well.

The anchors may be formed from metals, polymers, or other biocompatible materials having sufficient strength to remain attached to the valve annulus for indefinite periods after implantation. The valve assist leaflets will typically be formed from flexible materials which may be of the type used in prosthetic heart valves, such as tissues, e.g., pericardium which has been treated to promote stabilization, as well as various synthetic polymers. The valve assist leaflet may also be reinforced with a metal or polymeric a reinforcement structure attached over all or a portion of either or both surfaces of the leaflet.

In a second specific aspect of the present invention, a method for promoting valve coaptation in a patient comprises identifying a prolapsing valve in the patient, e.g., using conventional ultrasonic or other imaging techniques. A single prosthetic valve assist leaflet is implanted over a superior surface of a first native leaflet of the prolapsing valve. The single valve assist leaflet moves in unison with the first native valve leaflet and will coapt with a second native valve leaflet in response to blood flow through the valve. In this way, valve prolapse can be reduced and leakage minimized.

In some embodiments of the methods for promoting valve coaptation of the present invention, the native valve may be a cardiac valve, such a mitral valve or an aortic valve. In other embodiment, the native valve may a venous valve typically a peripheral venous valve.

Implanting may comprise implanting the single prosthetic valve leaflet in an open surgical procedure, but will more typically comprise advancing the single prosthetic valve leaflet endovascularly. transseptally, or transapically, as illustrated in detail below.

When introduced endovascularly. transseptally, or transapically, implanting usually comprises self-expanding an anchor coupled to the single prosthetic valve leaflet within the native valve annulus. The anchor may be expanded to fully circumscribe the valve annulus or may be expanded to partially circumscribe the valve annulus. In both cases, and particularly when the anchor partially circumscribes the annulus, the anchor may include one or more barbs or other tissue penetrating elements which penetrate the native valve annulus as the anchor expands to assist in fixing the anchor to the annulus. Alternatively, in some cases, implanting may comprise suturing an anchor coupled to the single prosthetic valve leaflet to the native valve annulus.

In a third specific aspect of the present invention, a method for delivering a prosthetic valve coaptation assist device to a native valve site comprises providing the prosthetic valve coaptation assist device having an anchor and a single prosthetic valve assist leaflet constrained within a delivery device. The delivery device is advanced to the native valve site, and the prosthetic valve coaptation assist device is deployed from the delivery device at the native valve site. The prosthetic valve coaptation assist device has an anchor which expands within an annulus of the native valve to locate the single prosthetic valve assist leaflet over a superior surface of a native valve leaflet. The single valve assist leaflet moves in unison with the first native valve leaflet and will coapt with a second native valve leaflet in response to blood flow through the valve. In this way, valve prolapse can be reduced and leakage minimized.

In some embodiments of the method for delivering a prosthetic valve coaptation assist devices, the native valve may be a cardiac valve, such a mitral valve or an aortic valve. In other embodiment, the native valve may a venous valve typically a peripheral venous valve.

Advancing may comprise advancing the single prosthetic valve leaflet endovascularly. transseptally, or transapically, as illustrated in detail below.

Deploying will typically comprise releasing prosthetic valve coaptation assist device from constraint so that the anchor self-expands within the native valve annulus to hold the single prosthetic valve leaflet in place over the first native valve leaflet. The anchor may self-expand to fully circumscribe the valve annulus. Alternatively, the anchor may self-expand to partially circumscribe the valve annulus. In either case, and particularly in the case of the partial expansion, the anchor may include one or more barbs which penetrate the native valve annulus as the anchor self-expands.

BRIEF DESCRIPTIONS OF THE DRAWINGS

The Figures of the present application use the following reference numbers:

(00) leaflet assist device
(01) device ring
(02) device body
(03) posterior mitral leaflet
(04) anterior mitral leaflet
(05) left ventricle
(06) left atrium
(07) device leaflet overlap
(08) chordae tendineae and papillary muscle
(09) inter-atrial septum
(10) inter-ventricular septum
(11) device strap
(12) guiding catheter with anchor system
(13) delivery-catheter
(14) anchor port
(15) 4x orifice for attachment of the guidance catheter
(16) guiding catheter of the median anchor system
(17) anchor nail
(18) guiding catheter of the guiding nail
(19) guiding nail
(20) guiding catheter with anchor system
(21) myocardium
(22) median anchor
(23) lateral anchors
(24) delivery catheter for coupling elements
(25) steerable delivery catheter for coupling elements -continued

(26) coupler drive element
(27) device strap spring element
(28) device strap hinge
(29) coupling locations
(30) perimeter stiffener
(31) flexure stiffener
(32) guide element sheath
(33) guide element lock
(34) screw anchor element
(35) screw anchor drive
(36) guide element sheath slot
(37) guide element lock feed-through
(38) anchor drive slot
(39) helical screw element
(40) locking slot
(41) steering wire
(42) screw anchor system
(2900) leaflet assist or repair device
(2901) connector
(3000) leaflet assist or repair device
(3001) connector
(3100) leaflet assist device
(3101) curved section
(3103) arrow
(3105) directionally sensitive edge stiffener
(3110) directionally sensitive center stiffener
(3115) slice or space
(3120) raised section
(3121) compliant direction
(3123) arrow
(3125) stiff direction
(3200) leaflet assist device
(3201) connector
(3300) leaflet assist device
(3301) leaflet
(3400) leaflet assist device
(3401a) first leaflet
(3401b) second leaflet
(3403) directionally sensitive stiffener
(3500) leaflet assist device
(3530) periphery
(3600) leaflet
(3630) periphery
(3700) leaflet assist device
(3710) sheet
(3720) attachment
(3800) coaptation device
(3810) sheet
(3820) attachment
(3840) tether
(3850) spindle bead
(3900) coaptation device
(3920) attachment
(3940) tether
(3950) spherical shaped bead
(AML) anterior mitral leaflet
(APR) annuloplasty ring
(CT) chordae tendineae
(FPL) failed prosthetic leaflet
(LA) left atrium
(LV) left ventricle
(MC) mitral clip
(MV) mitral valve
(MVA) mitral valve annulus
(NMV) native mitral valve
(PML) posterior mitral leaflet
(PMV) prosthetic mitral valve
(PV) pulmonic valve
(RA) right atrium
(RV) right ventricle
(TV) tricuspid valve
(ST) septum FIG. 1 illustrates a first embodiment of a prosthetic leaflet assist device constructed in accordance with the principles of the present invention.

FIGS. 9, 10A, 10B, and 11 illustrate alternative device strap designs.

Figure 12:
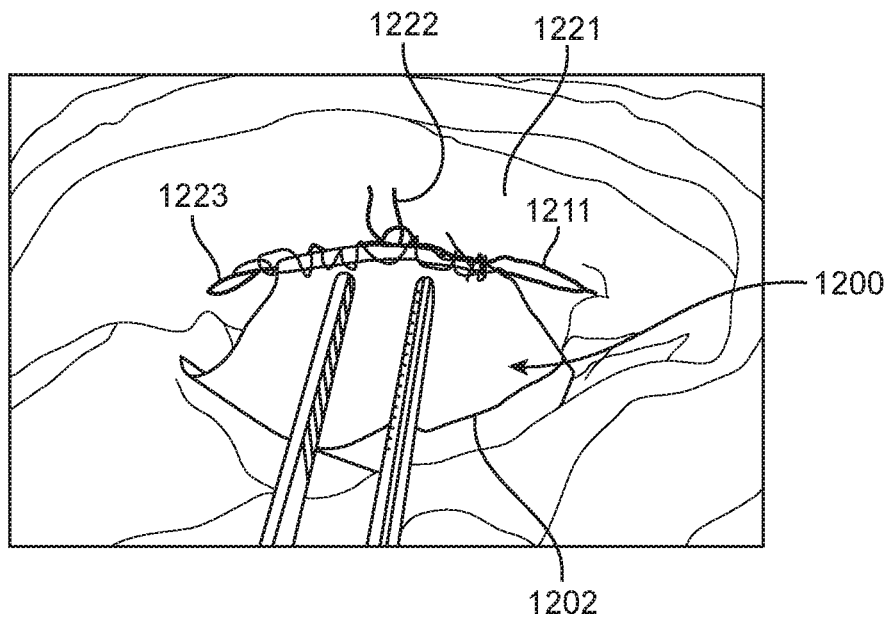

FIG. 12 is a perspective view of an alternate mitral assist device viewed from a left atrium after deployment in a pig heart.

Figure 11:
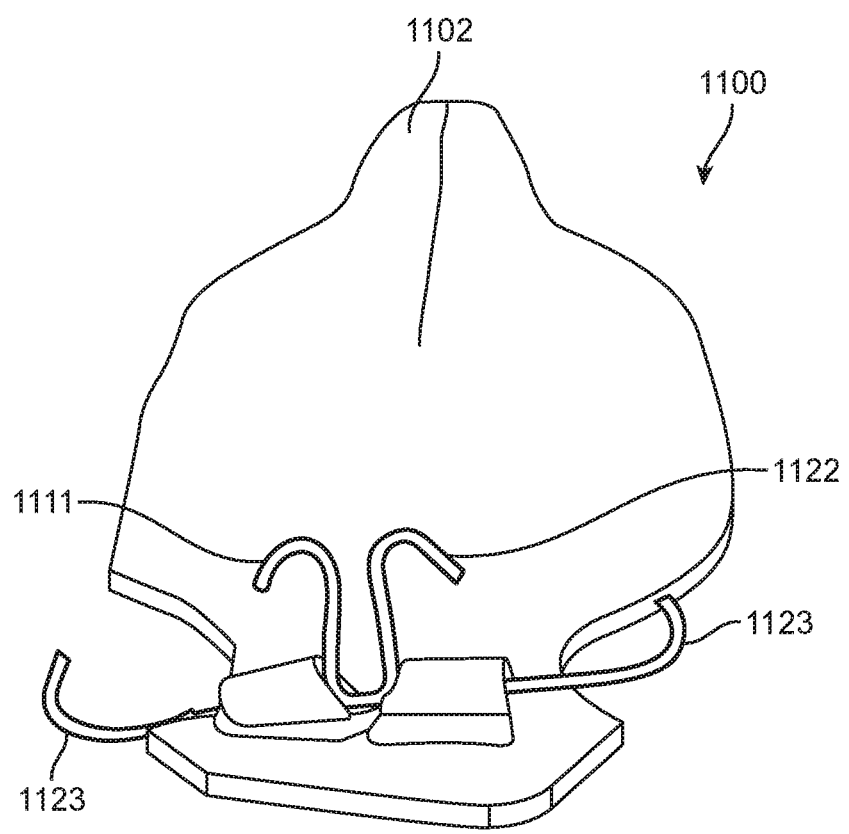
Figure 13:
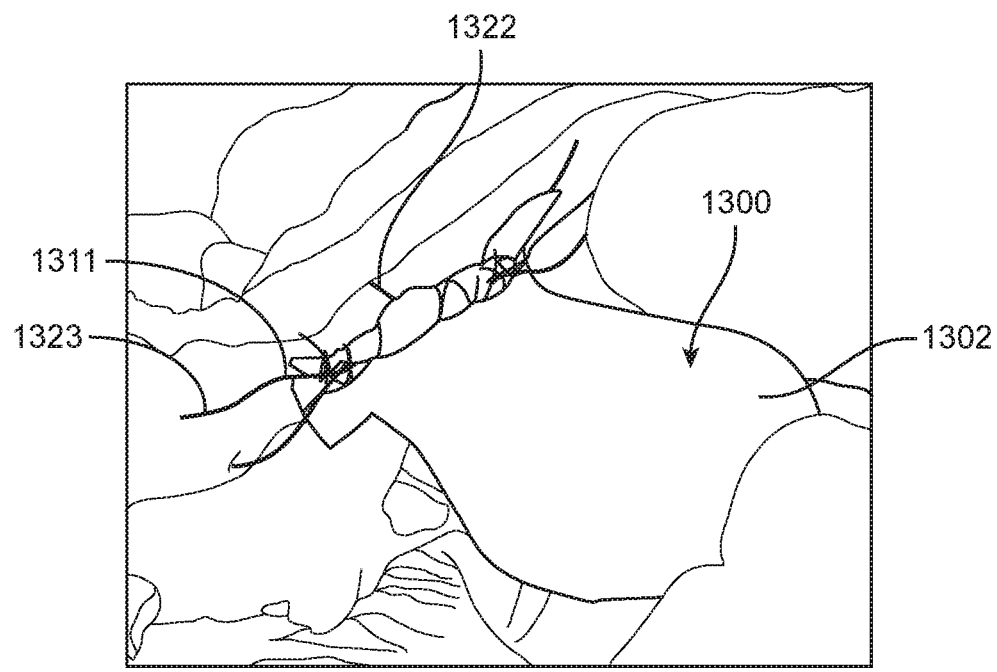

FIG. 13 is a perspective view of a further alternative mitral assist device similar to that shown in FIG. 11 shown in a deployed state.

Figure 14:
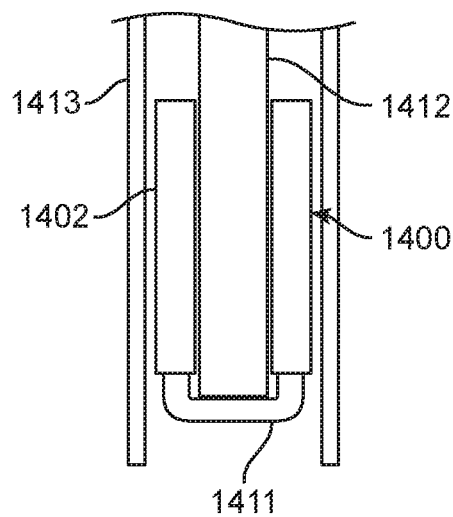
Figure 15:
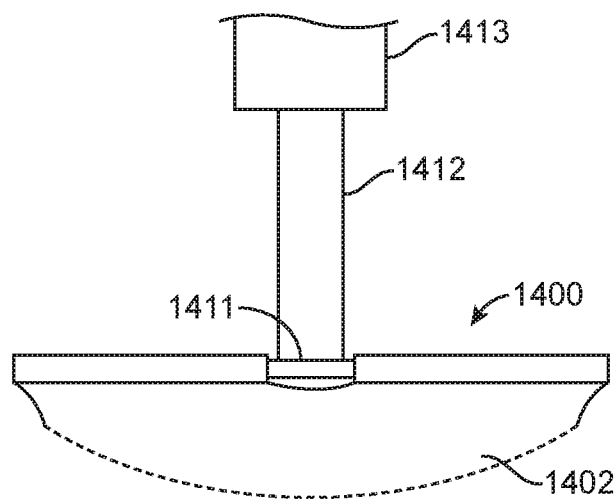
Figure 16:
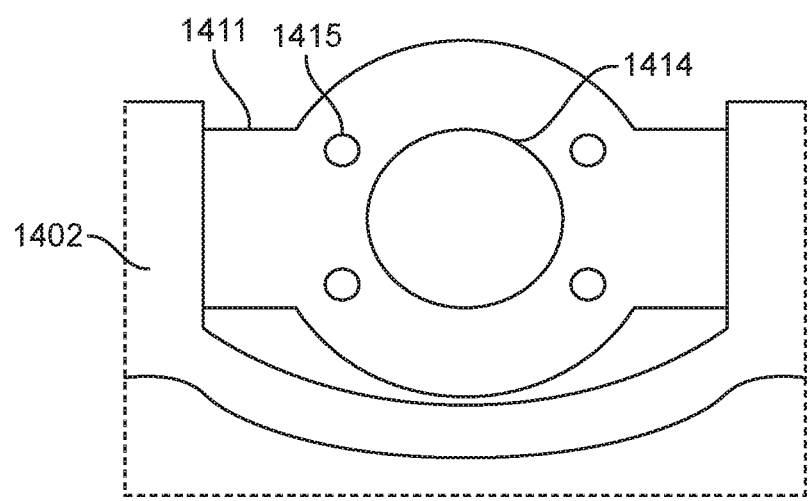

FIGS. 14, 15, and 16 depict aspects of yet another alternative leaflet assist device and deployment system including a guide catheter.

Figure 17A:
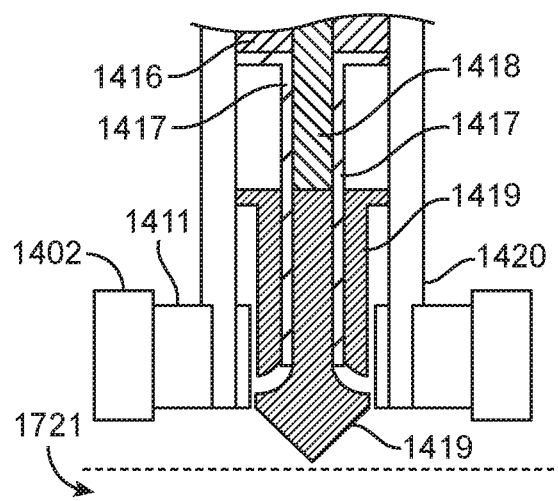

FIG. 17A illustrates a side sectional view of an anchoring portion of the mitral assist device after the assist device has been released from a delivery catheter but prior to activation of the anchor.

Figure 17B:
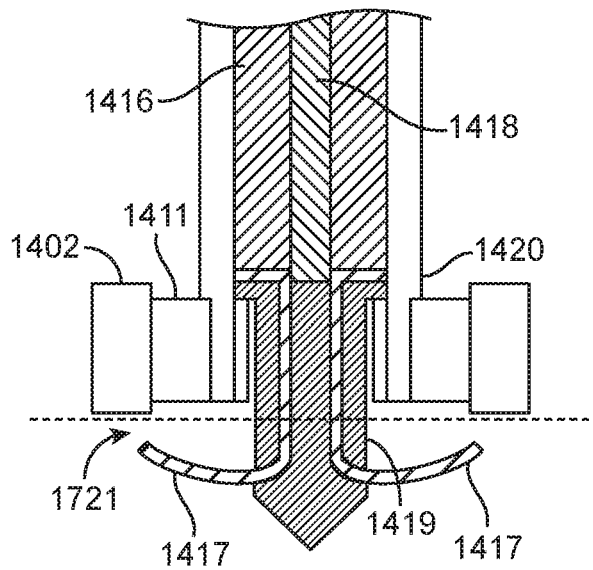

FIG. 17B illustrates the device of FIG. 17A after deployment of the anchor.

Figure 18:
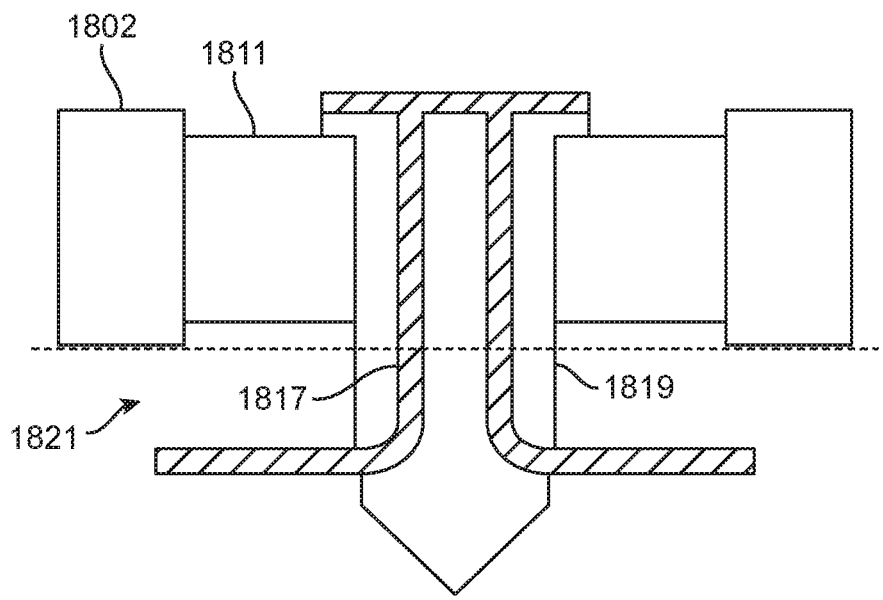

FIG. 18 is a cross-sectional view of an anchoring portion useful with the embodiments of FIGS. 14 through 17A and 17B illustrated in a fully deployed configuration.

FIGS. 19A, 19B, 19C, and 19D illustrate another alternative mitral assist device and delivery system including a delivery catheter visualized at various stages during a delivery cycle.

Figure 19A:
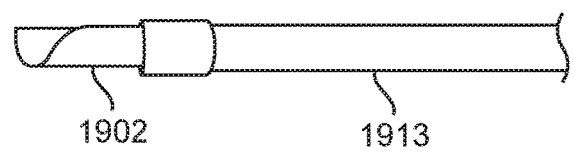
Figure 19B:
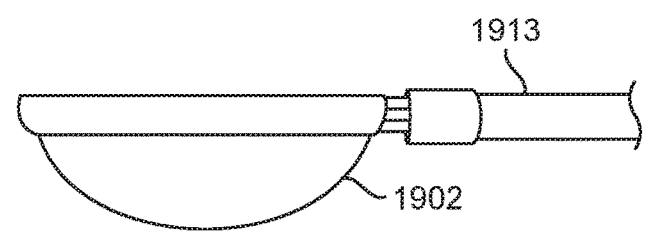
Figure 19C:
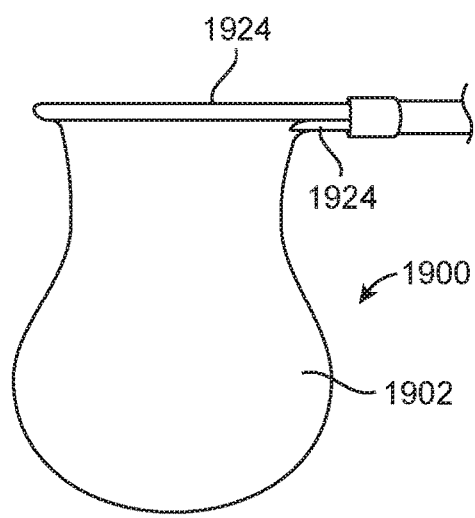
Figure 19D:
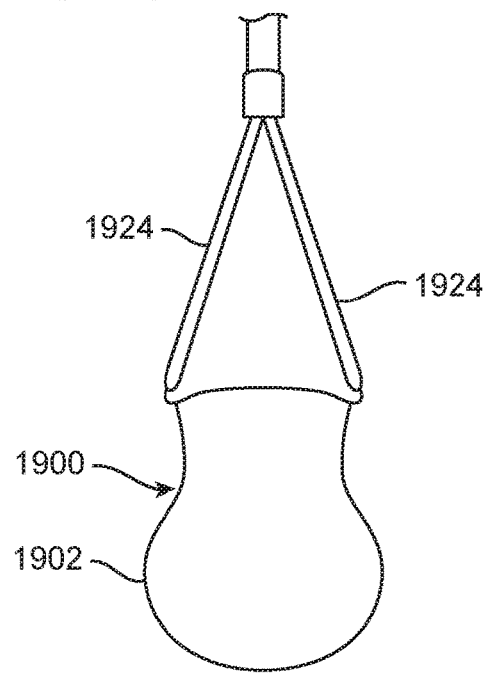
Figure 20:
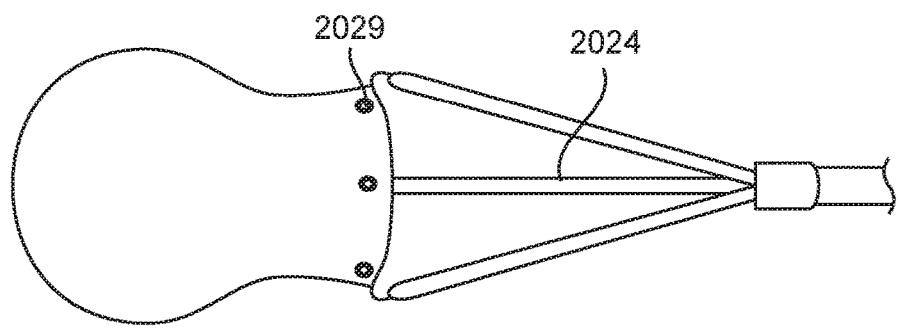

FIG. 20 illustrates a mitral assist device similar to that of FIG. 19 but carried on three coupling delivery catheters.

FIGS. 21A, 21B, 21C, and 21D illustrate an alternate embodiment of a coupling element that terminates in an anchoring mechanism which is used to affix the mitral assist device to a myocardium.

Figure 22:
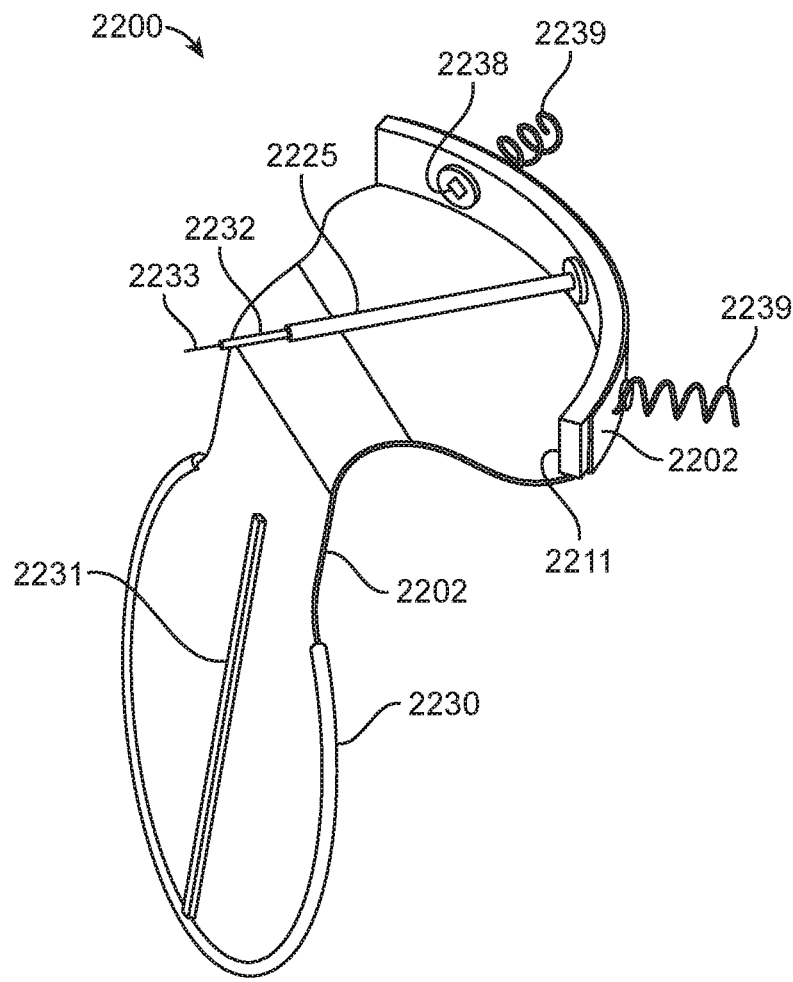

FIG. 22 illustrates a device formed of a molded material having a perimeter stiffener.

Figure 23A:
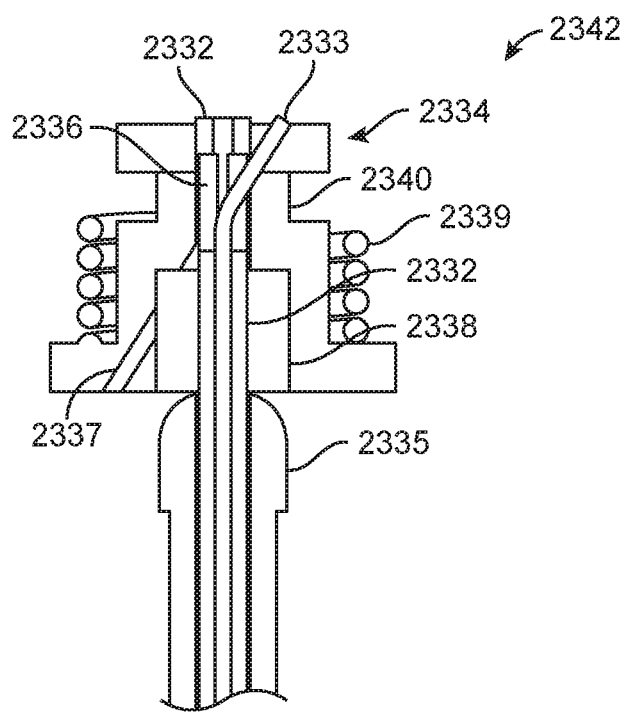
Figure 23B:
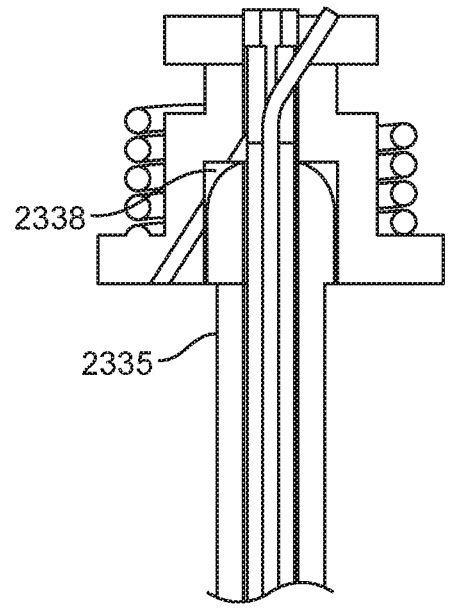

FIGS. 23A and 23B show a cross-section of a screw anchor system

Figure 23C:
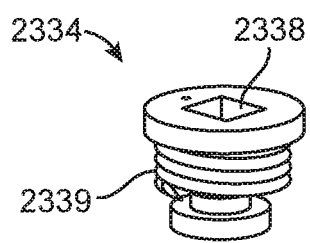
Figure 23D:
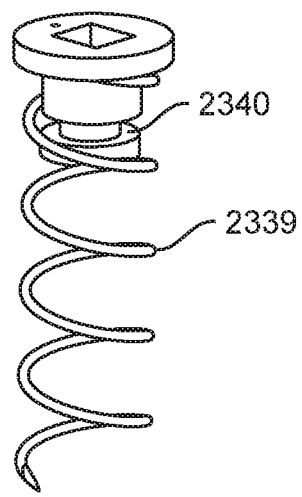

FIGS. 23C and 23D illustrate the delivery and operational configurations of screw anchor element of FIGS. 23A and 23B, respectively.

Figure 24:
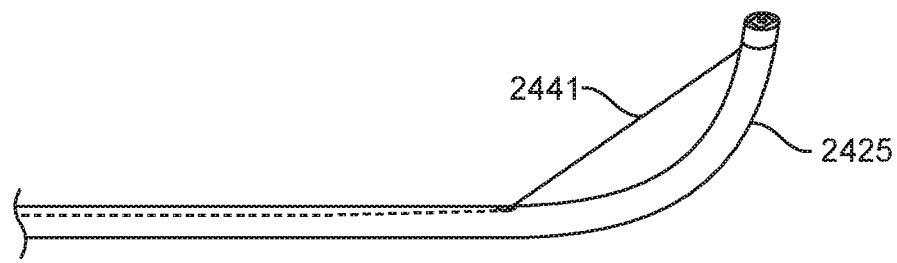

FIG. 24 shows an embodiment of a steerable delivery catheter for coupling elements.

Figure 25:
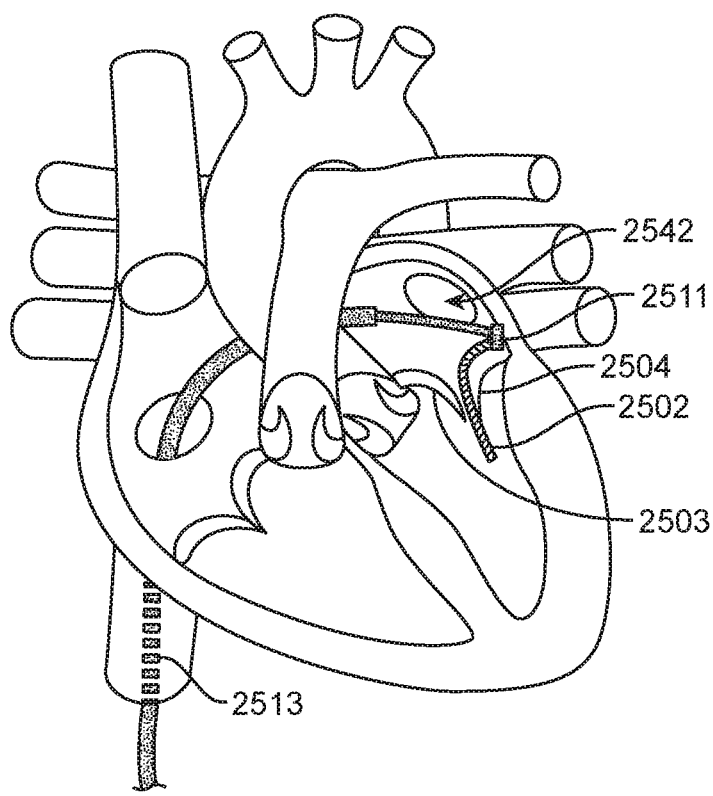

FIG. 25 shows a steerable delivery catheter delivering a device to a target area via an endovascular transseptal approach from an inferior vena cava.

Figure 26:
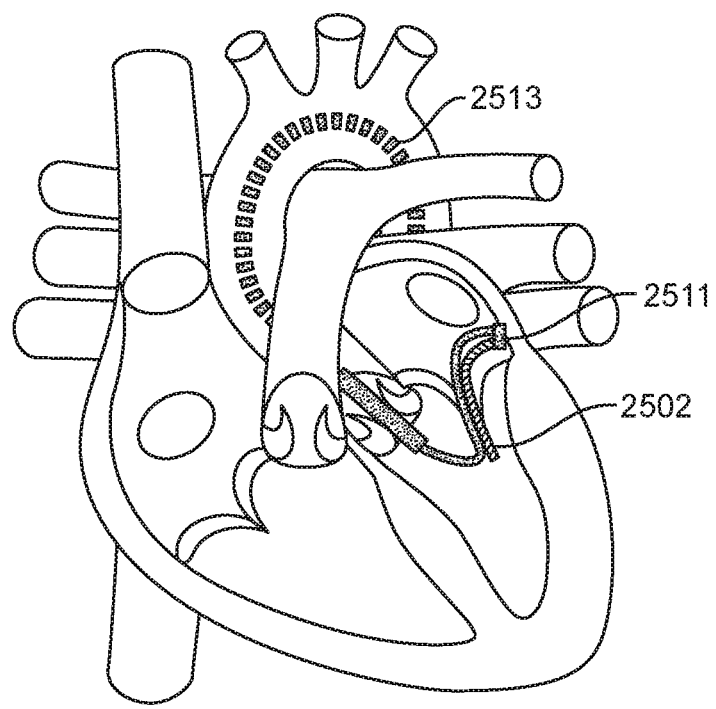

FIG. 26 shows a steerable delivery catheter delivering a device to a target area via an endovascular arterial delivery approach.

Figure 27:
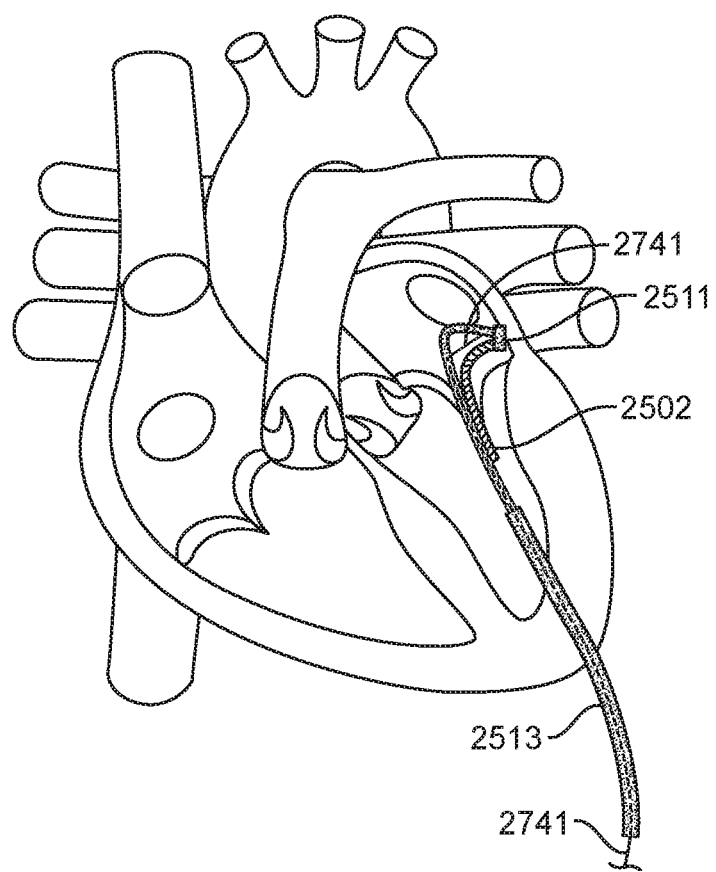

FIG. 27 shows a steerable delivery catheter delivering a device to a target area via a transapical approach.

Figure 28:
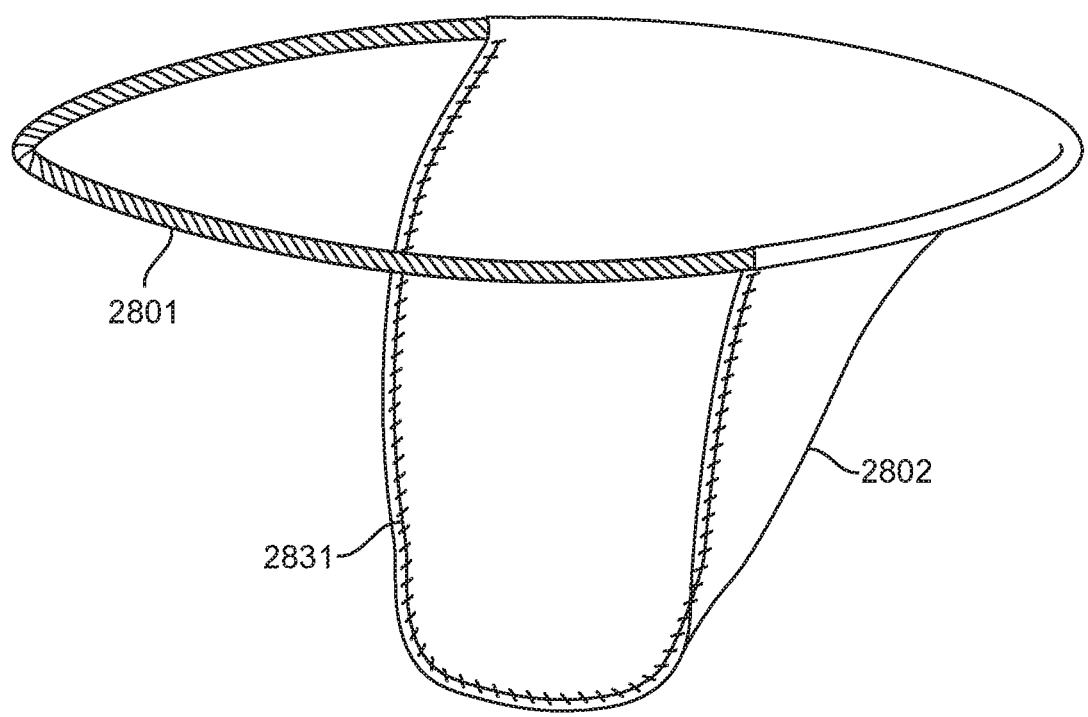

FIG. 28 illustrates a mitral assist device having flexible stiffening present in the perimeter of the mitral assist device body to minimize the upward displacement of the mitral assist device during mitral closure.

Figure 29:
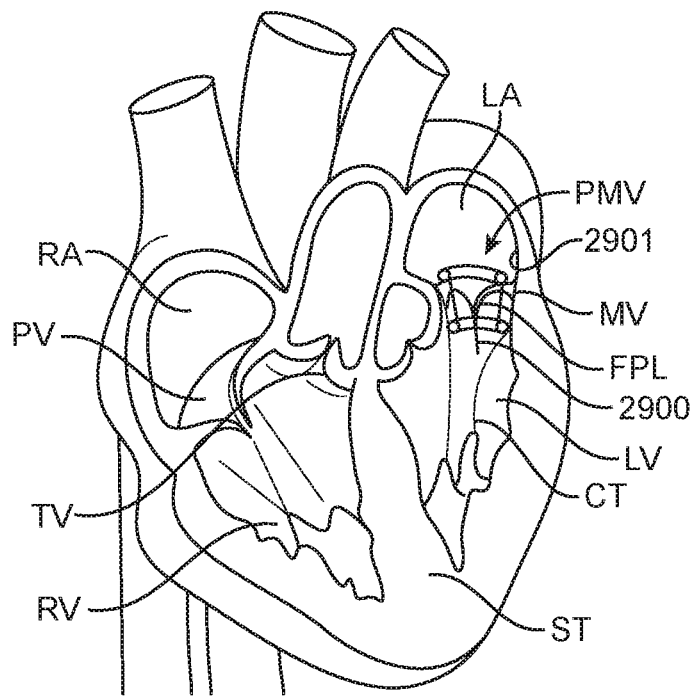

FIG. 29 shows a section view of a heart having a leaflet assist or repair device placed therein to assist or repair a defective prosthetic leaflet, according to many embodiments.

Figure 30:
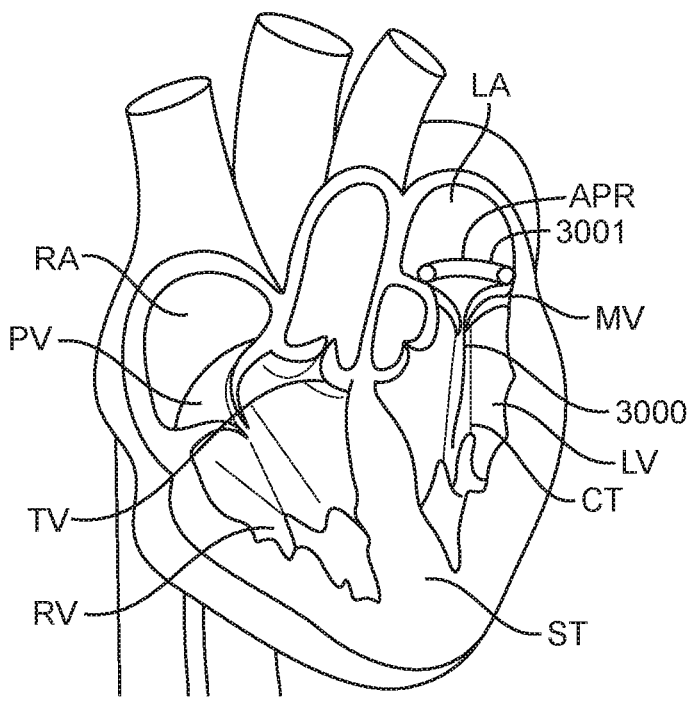

FIG. 30 shows a section view of a heart having a leaflet assist device placed therein to assist a previously placed annuloplasty ring, according to many embodiments.

FIGS. 31A, 31B, 31C, and 31D show a back perspective, a front perspective, and side views, respectively, of a leaflet assist device, according to many embodiments.

Figure 32A:
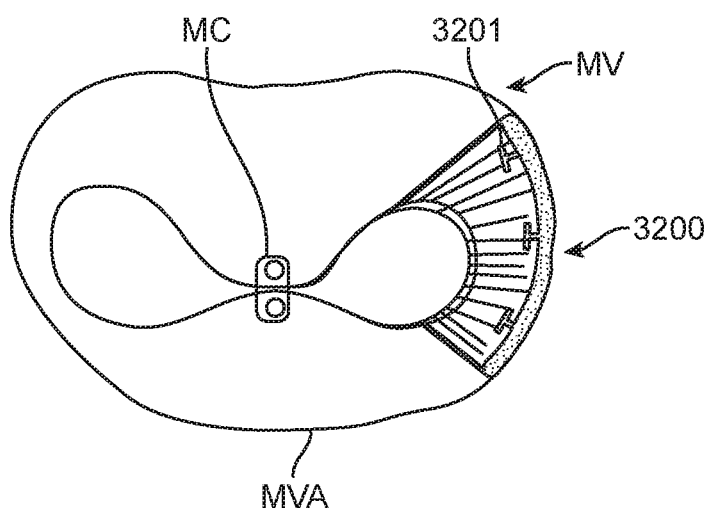
Figure 32B:
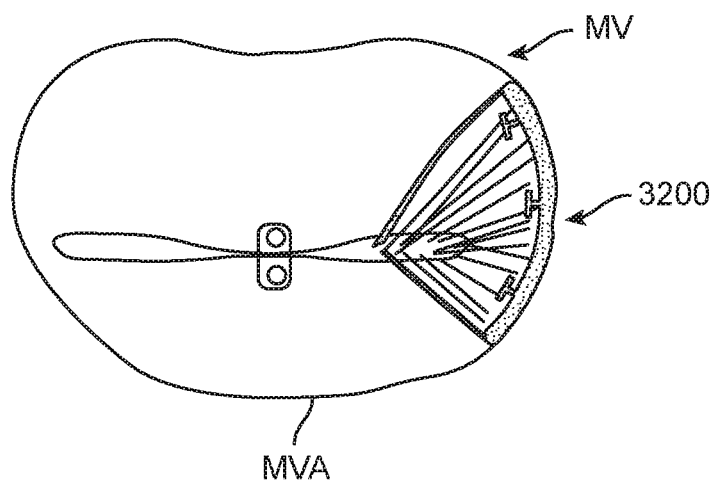

FIGS. 32A and 32B show top views of a mitral valve and mitral valve annulus having a leaflet fixation device and a leaflet assist device attached thereto, according to many embodiments.

Figure 33A:
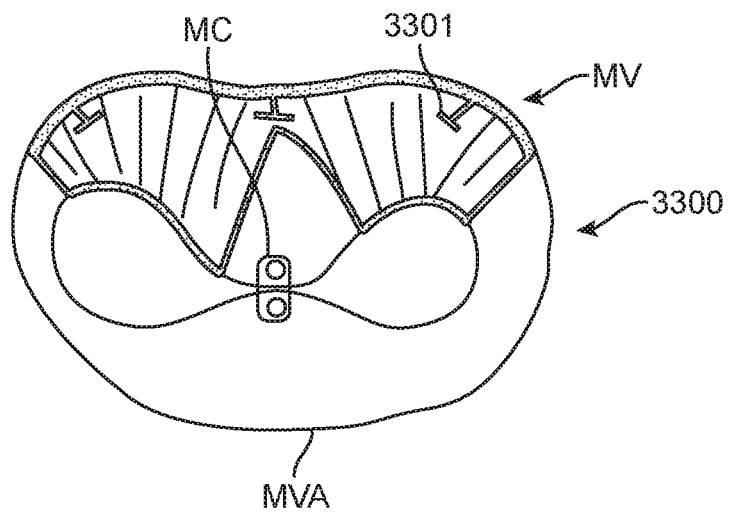
Figure 33B:
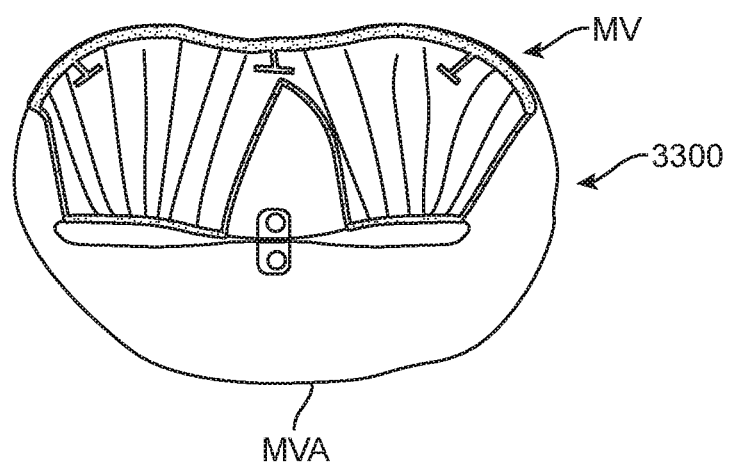

FIGS. 33A and 33B show top views of a mitral valve and mitral valve annulus having a leaflet fixation device and a leaflet assist device attached thereto, according to many embodiments.

Figure 34:
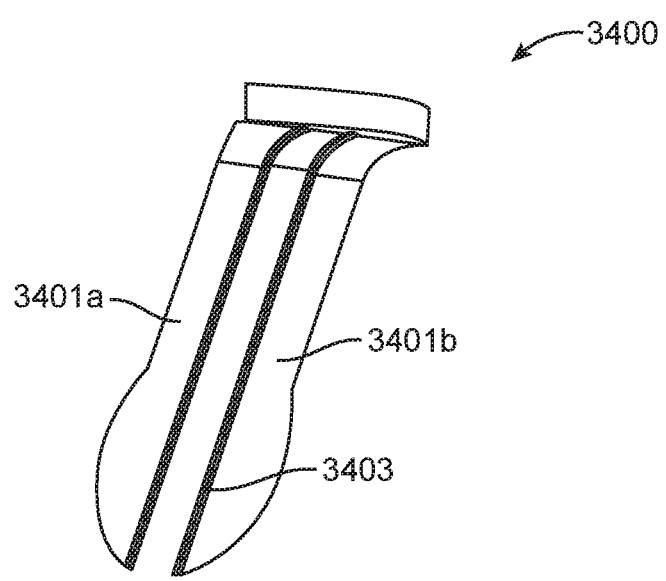

FIG. 34 shows a perspective view of a leaflet assist or repair device, according to many embodiments.

Figure 35:
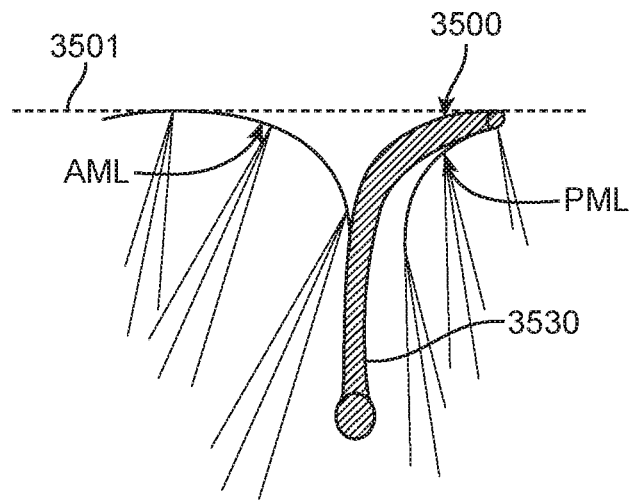

FIG. 35 shows a cross section of a mitral valve with a semi-flexible leaflet assist device placed thereover, according to many embodiments.

Figure 36:
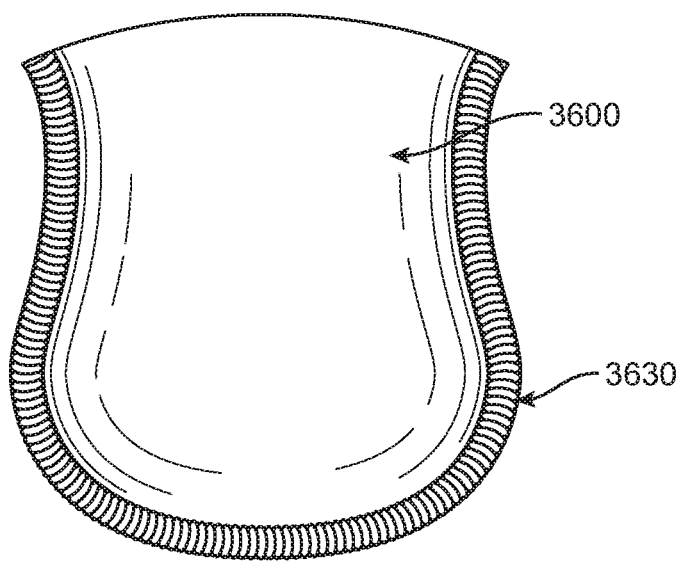

FIG. 36 shows a leaflet for leaflet assist devices, according to many embodiments.

FIGS. 37, 38, 39, and 40 show top views of mitral valves with leaflet assist device attached, according to many embodiments.

DESCRIPTION OF THE INVENTION

Figure 1:
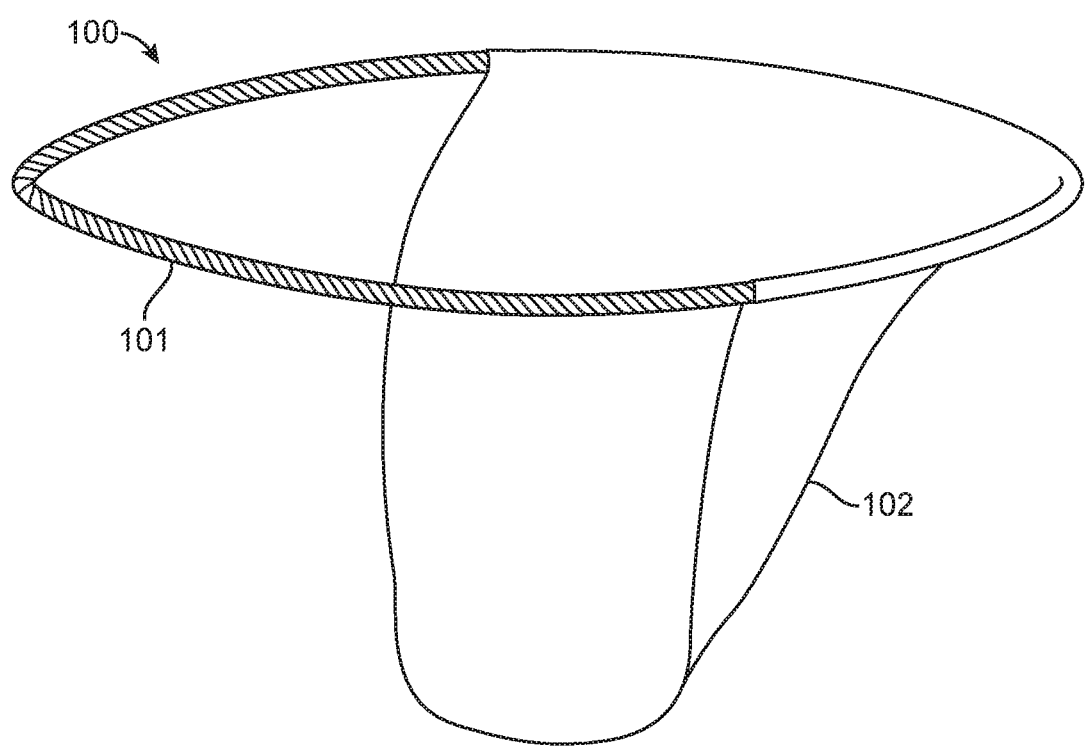

FIG. 1 depicts a surgically and or percutaneously deliverable prosthetic leaflet assist device 100 having a device ring 101 which serves as an anchor for attaching to tissue near or at the mitral or other valve annulus and a device body or prosthetic leaflet 102 for improving the function of a native (e.g., mitral) leaflet. The leaflet material may be selected from any of the synthetic biocompatible polymers such as Dacron or polyurethane, or treated natural fixed materials such as pericardial or and other material known in the art for use in implantable valves. The device ring is generally made of metal (e.g., Nitinol) or a polymer such as polyurethane. In some embodiments the leaflet is sutured to the ring as when the leaflet is comprised of a natural fixed material. When the leaflet is comprised of a polymeric material it may be sutured, molded, or affixed through the use of adhesive to the device ring. Alternatively the device ring may be threaded through the leaflet. Flexible leaflet 102 interfaces with the native leaflet.

Figure 2A:
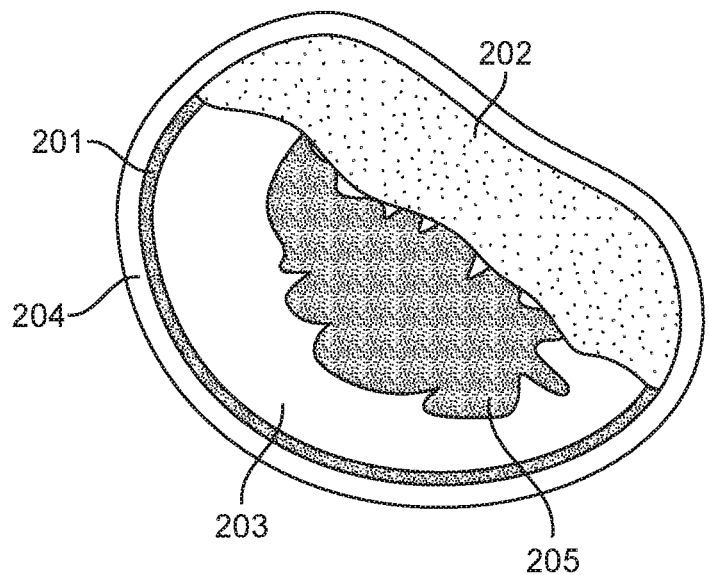
FIGS. 2A and 2B illustrate a prosthetic leaflet assist device implanted in a mitral valve mitral position as viewed from a left atrium during mid-diastole (FIG. 2A) and mid-systole (FIG. 2B).
Figure 2B:
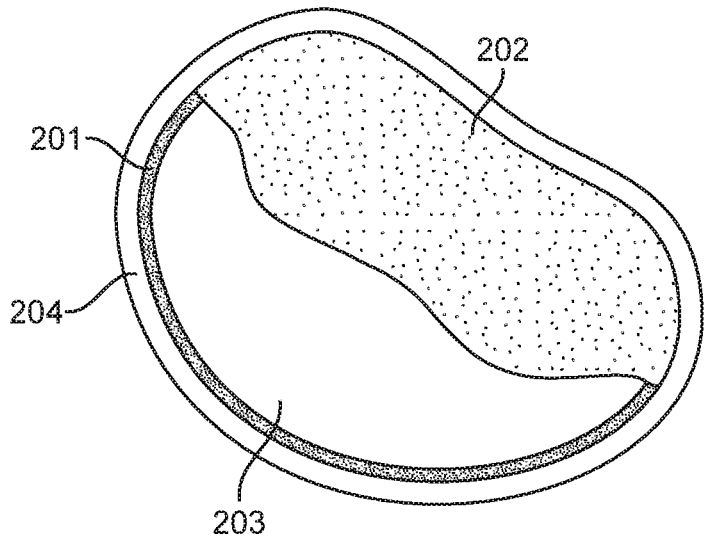

FIG. 2A depicts the device in the mitral position as viewed from a left atrium during mid diastole. The device ring 201 interfaces with the annulus fibrous sinister at the perimeter of the anterior mitral leaflet 204 and the left ventricle 205 can be seen through the open valve. The device leaflet 202 sits opposite the posterior leaflet 203 and over the anterior mitral leaflet 204. FIG. 2B depicts the device during mid systole.

Figure 3:
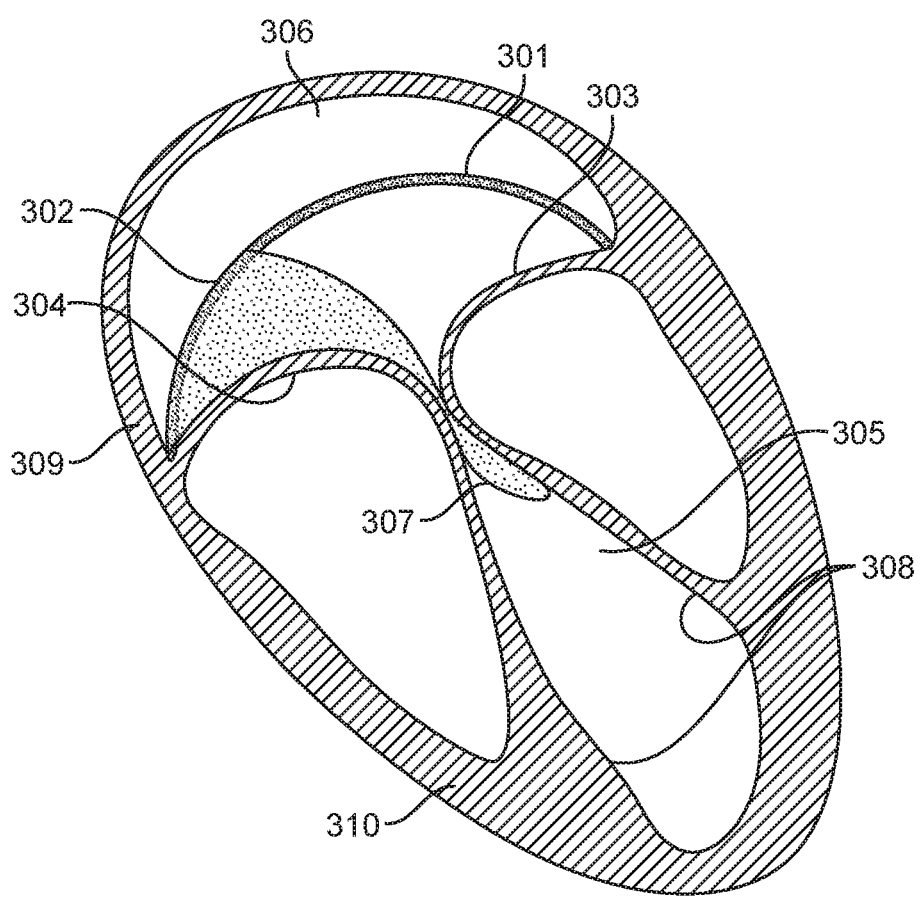
FIG. 3 illustrates the prosthetic leaflet assist device implanted in a mitral valve as viewed from a left atrium during mid-diastole from a side view.

FIG. 3 illustrates the device in mitral valve position during mid diastolic from a side view. Device ring 301 in the left atrium 306 holds the device body or leaflet 302 opposite the posterior mitral leaflet 303 and over the anterior mitral leaflet 304, the leaflet 302 extends into the left ventricle 305 and is captured at overlap 307 between the two mitral leaflets. Chordae tendineae and papillary muscle 308 restrain the natural leaflets. The inter-atrial septum 309 and the inter-ventricular septum 310 are also illustrated.

Figure 4:
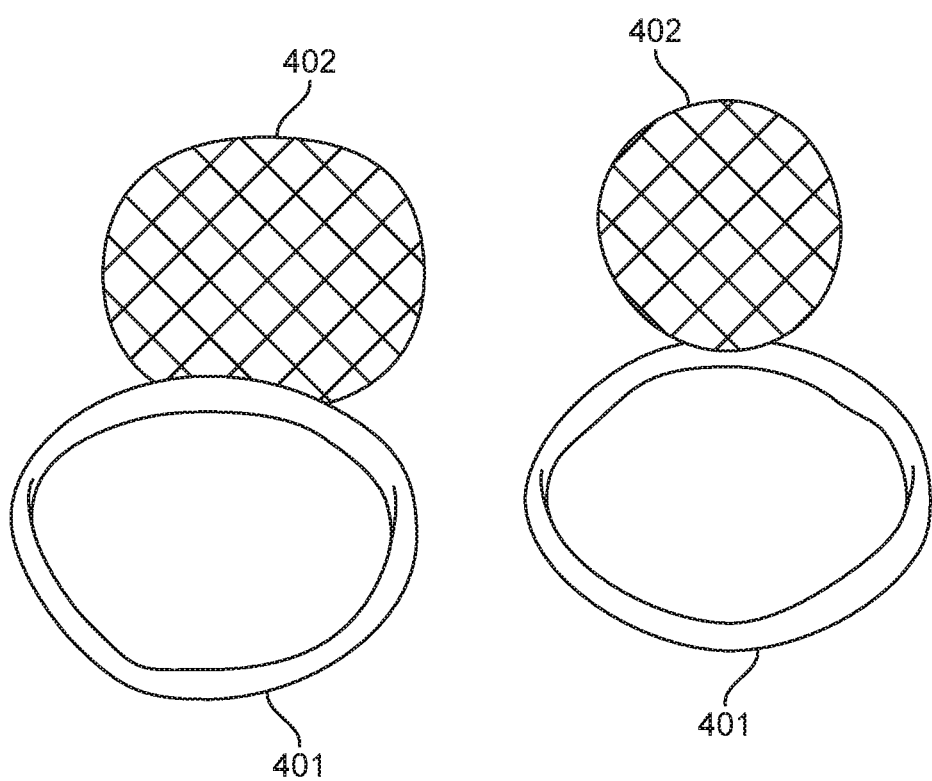
FIG. 4 is a perspective view of a pair mitral assist device prototypes fabricated from a polymer.

FIG. 4 shows two mocked up variations of a mitral assist device fabricated of a polymer. As depicted the device bodies 402 are affixed to polymer rings 401. Alternatively, the device rings 401 and the device bodies 402 may be molded as a complete device. As illustrated the device bodies are crafted in two different sizes to accommodate different size native mitral valves.

Figure 5A:
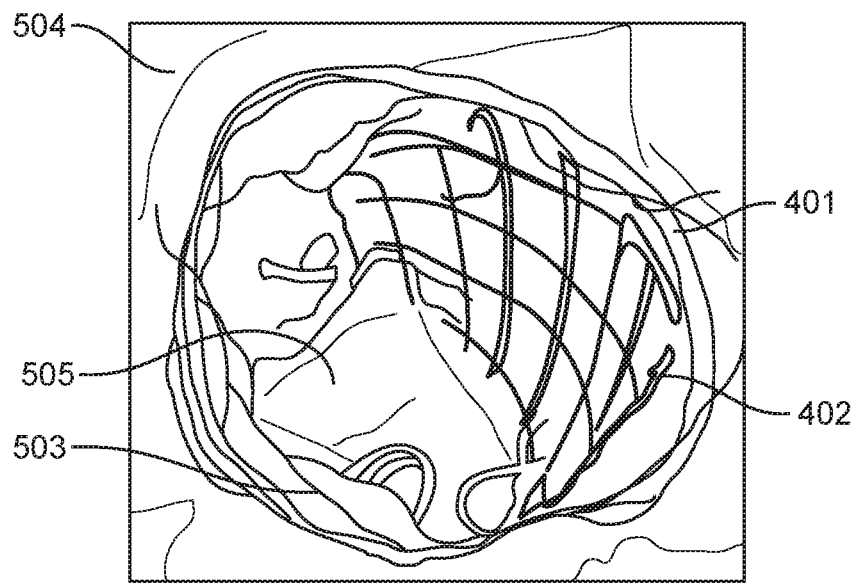
FIGS. 5A and 5B are perspective views of a reinforced polymeric prosthetic leaflet assist device taken from a left pig atrium during simulated mid-systole (FIG. 5A) and mid-diastole (FIG. 5B).
Figure 5B:
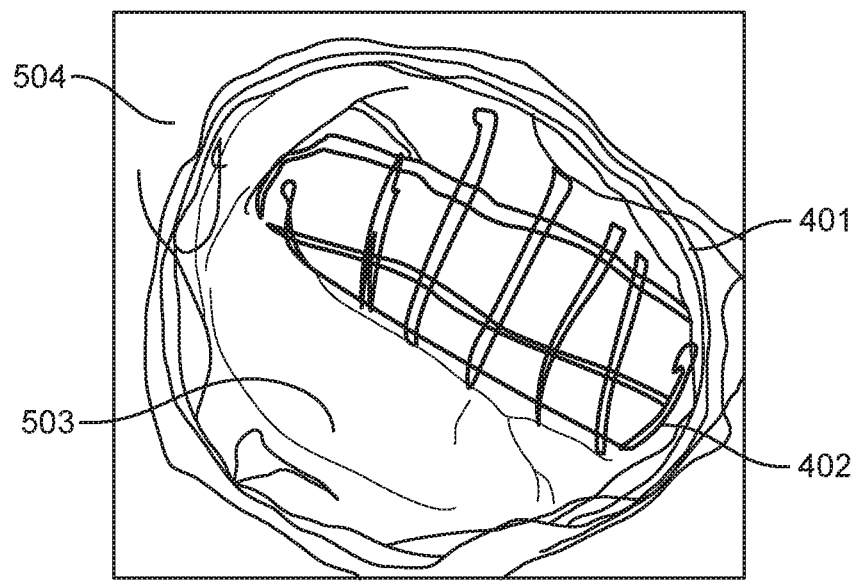

FIG. 5A shows a top view from the left atrium during mid diastole of a mitral assist device comprising device ring 401 and device body 402 sutured into the mitral annulus fibrosus sinister above mitral leaflet 504 of a pig heart. The mitral assist device is oriented such the device body sits over the anterior mitral leaflet opposite the posterior mitral leaflet 503. The left ventricle 505 is visible through the open valve. FIG. 5B shows the same valve during mid diastole.

Figure 6A:
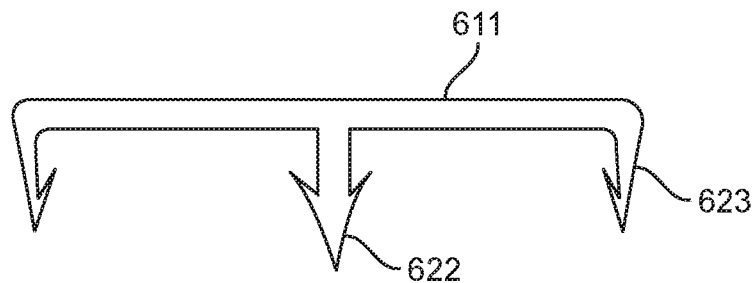
FIG. 6A illustrates a strap for affixing a leaflet assist device to a mitral annulus.
Figure 6B:
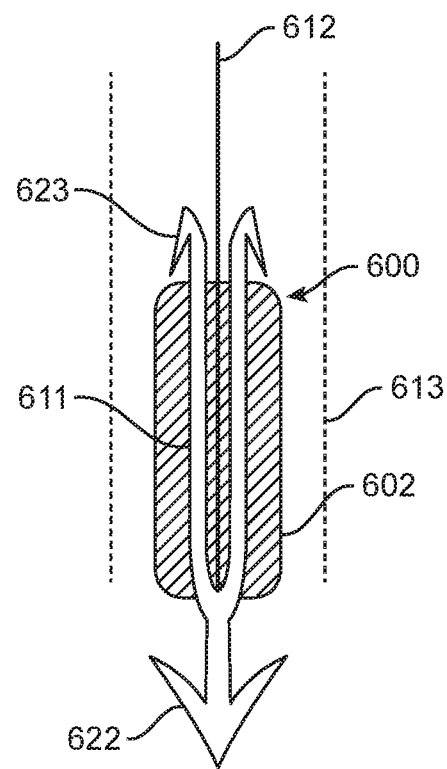
FIG. 6B illustrates the leaflet assist device of FIG. 6A compressed in a catheter for percutaneous delivery.

FIG. 6A illustrates a device strap 611 which provides for an alternate means for affixing a leaflet assist device to the mitral annulus. This arrangement does not require the valve ring to be sutured to the annulus thereby facilitating a simpler percutaneous means of attaching the leaflet assist device. The device strap 611 is comprised of a median or medial anchor 622 and two lateral anchors 623. The anchors are "barbed" structures designed to puncture the heart tissue and lock the device strap in place. FIG. 6B depicts a leaflet assist device 600 configured for percutaneous delivery comprising the anchor strap 611. Device body 602 is wrapped around the device strap 611 which has been folded in half at the median anchor 622. The mitral assist device is constrained in a delivery catheter 613 and at the distal end of a delivery catheter which may be affixed to or separate from the guide catheter 612. When it is affixed a means of detachment is provided for, such as the use of an electrolysible junction as known in the art for the release of arterial stents. The strap is comprised of Nitinol or other material of appropriate resilience. Upon delivery to the atrium, the device 600 is pushed from within the delivery catheter 613 with the guiding catheter 612 forcing median anchor 622 into the mitral annulus tissue. The delivery catheter is then moved proximally to release the lateral anchors 623 and valve body 602. As the lateral anchors unfold on release they bury themselves into the annulus tissue.

Figure 7A:
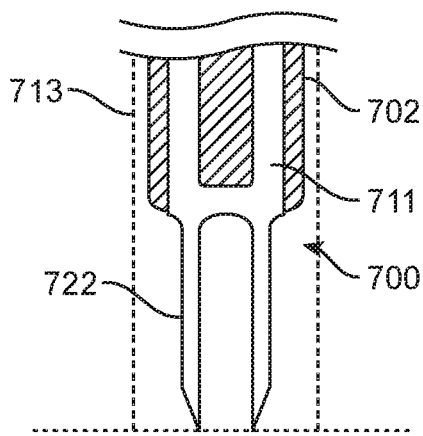
FIG. 7A illustrates a distal portion of a valve assist device configured for delivery within a delivery catheter.
Figure 7B:
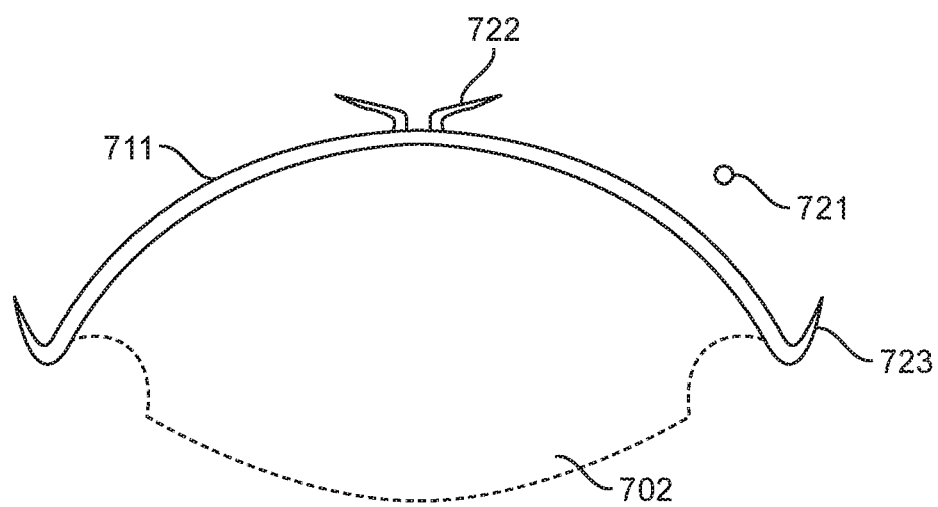
FIG. 7B illustrates the leaflet assist device of FIG. 7A in its deployed configuration.

FIG. 7A illustrates a distal portion of a valve assist device 700 as configured for delivery within a delivery catheter 713. The device strap 713 is bent at its midpoint between the two prongs comprising the median anchor 722 during delivery. As the device is forced into myocardium 721 and released from the delivery catheter 713, the median anchor prongs 722 spread locking the median anchor into the myocardium 721, lateral prongs 723 puncture myocardium. FIG. 7b illustrates the leaflet assist device 700 in its deployed configuration.

Figure 8:
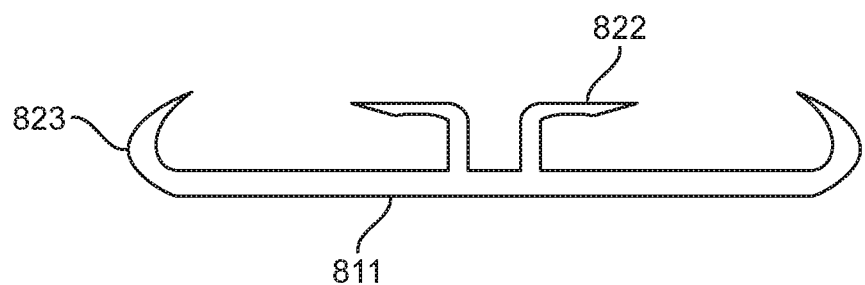
FIG. 8 illustrates a device strap with median anchor elements and lateral anchor elements on an anchor strap.

FIG. 8 illustrates a version of a device strap wherein median anchor elements 822 and lateral anchor elements 823 are comprised on anchor strap 811. The device strap of FIG. 8 is short enough that it does not require a curved shape to match the annulus.

Figure 9:
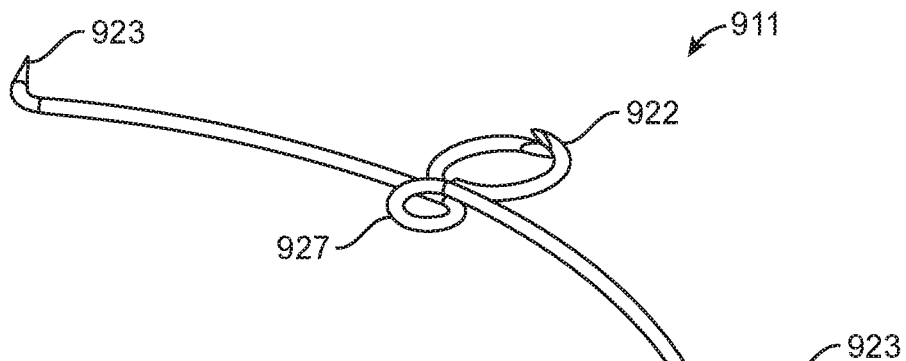

FIGS. 9, 10A, 10B, and 11 represent alternative designs for a device strap. FIG. 9 comprises a device strap fabricated from wire (such as Nitinol or similar material capable of sustaining high strains). Median anchor elements 922 are comprised on the anchor strap 911 on spring element 927. When in a delivery configuration, lateral anchors 923 are pulled together, such that they point away from themselves, and spring element 927 is compressed opening the medial anchor elements. During delivery the open median anchors are pushed against the myocardium and then the delivery catheter is pulled back releasing lateral anchors 923 which, in turn, allows the median anchor elements to close thereby gripping the tissue. Upon release form the delivery catheter, lateral anchors 923 additionally swing into a position such that they penetrate into the myocardial tissue.

Figure 10A:
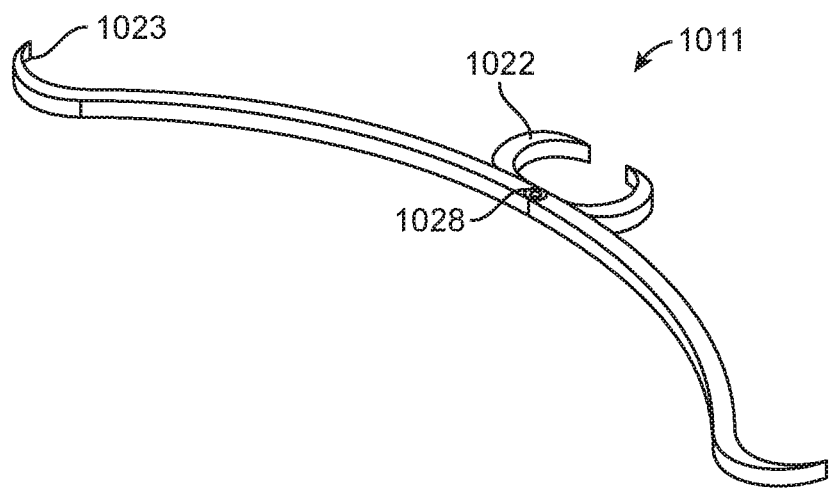
Figure 10B:
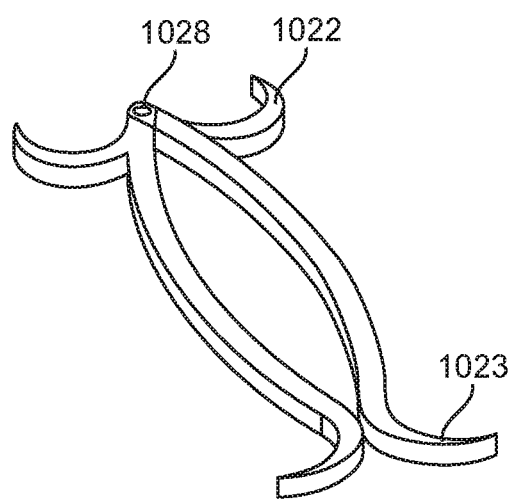

FIGS. 10A and 10B depict an alternate device strap 1011 in a delivered configuration as in FIG. 10A, and a deliverable configuration as in FIG. 10B. The device strap 1011 comprises a hinge element 1028 at the center of the median anchor elements 1022. The hinge element in some embodiments comprises a locking mechanism such that, upon shifting from the deployable configuration of FIG. 10B to the deployed configuration of FIG. 10A, the strap is locked in the deployed configuration with the median anchors locked in a grasping configuration. In some embodiments, a spring is used to urge the device strap into a deployed configuration upon release from a delivery catheter. In other embodiments, the device strap 1011 is manipulated and locked into the deployed configuration upon release from the delivery catheter.

FIG. 11 is an image of prototypical mitral assist device 1100. The device body 1102 is fabricated from a Dacron felt and the device strap 1111 from a stainless wire. In the image, the medial anchors 1122 are bent laterally 90 degrees form their delivery configuration for ease of viewing. The device strap 1111 held in place between layers of Dacron is affixed via glue as shown. In alternate embodiments, the layers may be sewn, solvent welded, heat welded, ultrasonically welded, or other suitable means.

In FIG. 12, an alternate mitral assist device 1200 is shown as viewed from a left atrium after deployment. In this embodiment, the device strap is comprised of a stainless steel wire similar to that of FIG. 11. In this configuration the lateral anchors are comprised of a pair of anchors on each end of the anchor strap 1211, and a pair of median anchors 1222 directed downward, all of which are hooked into the myocardial tissue 1221. In this embodiment the device body 1202 is affixed to the device strap 1211 by wrapping a portion of the device body around the device strap and locking it in place with suture. The lateral anchors 1223 have been compressed together to minimize their effect on restraining the motion of the impacted myocardial tissue.

In FIG. 13, another alternative mitral assist device similar to that shown in FIG. 11 is shown in the deployed state. The mitral assist device 1300 differs from that of FIG. 12 in that there is only one median anchor 1322 and lateral anchors 1323 have been spread to increase their purchase in the myocardium.

FIGS. 14 through 16 depict aspects of yet another alternative leaflet assist device 1400 and deployment system comprised in a guide catheter 1412. FIG. 14 illustrates the mitral assist device 1400 in a delivery configuration within a delivery catheter 1413 affixed to the distal end of guide catheter 1412 incorporating a delivery system. The valve body 1402 has been pleated to facilitate loading in the delivery catheter 1413. Guide catheter and delivery system 1412 are affixed to the mid-section or the device strap 1411. FIG. 15 depicts the mitral assist device 1400 during a deployment after release form the delivery catheter 1413.

FIG. 15 depicts the device strap 1411 after release from the delivery catheter in its unfolded deployment configurations where the valve body 1402 is unfurled also. The device strap is seen side-on still affixed to the guide catheter and delivery system 1412. FIG. 16 illustrates the central anchoring portion, and anchoring features, of the device strap 1411. This section of the device strap is used during delivery to affix the mitral assist device 1400 to the guide catheter and to anchor the mitral assist device to the myocardium on deployment. The anchor portion of the device strap comprises anchor port 1414 and guide catheter attachment features 1415.

FIG. 17A illustrates a side sectional view of the anchoring portion of the mitral assist device 1400 as configured after the assist device has been released from the delivery catheter and the device body has unfurled, but prior to activation of the anchor. The anchoring portion of the assist device is comprised of the device strap 1411 as described above and an activable anchor mechanism comprised of the following features: a nail guide driver 1418, one or more anchor nails 1417, a nail guide 1419, and an anchor nail drive 1416. The section illustrated comprises a section where the anchor nails pass through the guide. These all may be comprised within the guide catheter 1420 affixed to the device strap 1411 at guide catheter attachment features 1415. As illustrated, the guide catheter has been manipulated to point the mechanism towards the myocardium 1721 at a point near or at the mitral valve annulus. FIG. 17B illustrates the device after deployment of the anchor. Deployment of the anchor after proper alignment as depicted in FIG. 17 is accomplished as follows. Anchor guide nail driver 1418 and anchor nail drive 1416 are simultaneously pushed out of the guide catheter 1420 into the myocardial tissue until the guide nail 1419 has seated against the device strap 1411. Anchor nail driver 1416 is then pushed distally forcing the anchor nail forward through the nail guide 1419 and into the myocardium. The anchor nail is deformed as it passes through the nail guide thereby locking the anchor nail in the myocardial tissue.

A cross section of the anchoring portion of an embodiment similar to that of FIGS. 14 through 17A and 17B is illustrated in its fully deployed configuration in FIG. 18. In this embodiment, only one driver is required to actuate both the guide nail and the anchor nail. The mechanism relies on the increased force required to actuate the anchor nail vs. the penetrating the myocardium with the anchor assembly. During deployment, the anchor assembly, comprised of the nail guide 1819 and the anchor nail 1817, is pushed into the myocardium until the anchor assembly seats itself against the top surface of the of the device strap 1811. At this point, the anchor nail prongs are straight and are contained within the straight portions of the nail guide. Upon seating, and therefore penetrating the myocardium, the force of actuation is increased and the anchor nail 1817 is pushed through the nail guide thereby deforming the distal ends of the anchor nail as shown in FIG. 18. The cross section shown in FIG. 18 is rotated off of the cross section incorporating the attachment locations for the delivery catheter.

FIGS. 19A through 19D illustrate another alternative mitral assist device and delivery system comprised in a delivery catheter visualized at various stages during a delivery cycle. FIG. 19A illustrates the distal end of the delivery system with the mitral assist device body 1902 rolled around a set of delivery coupling elements (not visible), partially pushed out of the delivery catheter 1913. In FIG. 19B, the mitral assist device body 1902 has been completely pushed out of the delivery catheter 1913 and partially unrolled. In FIG. 19C, the mitral assist device 1900 illustrated is completely unrolled and tethered to coupling elements 1924. The mitral assist device 1900 is oriented at 90 degrees to the delivery catheter at this time and delivery coupling elements 1924 are visible. In FIG. 19D, the mitral assist device 1900 has been rotated by 90 degrees by withdrawing the delivery catheter relative to the mitral assist device or pushing the coupling elements further out of the delivery catheter and then equalizing the length of the coupling elements delivered from the delivery catheter. In this fashion, the orientation of the mitral assist device may be adjusted through a range of angles to better facilitate alignment with the mitral valve annulus prior to affixing it in place.

FIG. 20 illustrates a mitral assist device similar to that of FIG. 19 but carried on three coupling delivery catheters 2024; the device is then affixed in place via anchoring elements at anchor locations 2029 using an anchor installation tool (not shown).

The device of FIGS. 19 and 20 may be affixed in place by a number of different means. These include but are not limited to any of the following. The device may be placed appropriately within the mitral valve followed by placement of a mitral annuloplasty band (not shown). The annuloplasty band is then affixed in place locking the mitral assist device between the annuloplasty band and the mitral wall. One such band useable in this fashion is the Valtech Cardioband available from Edwards Lifesciences Corp. of Irvine, Calif. Alternatively, anchoring elements may be delivered via a second delivery catheter and used to anchor an attachment edge of the mitral assist device to the myocardium. Anchor elements may be but are not limited to any of the following configurations: helical anchors as described by Rosenman U.S. Pat. No. 6,478,776 but including a cap; helical anchors as described by Gross U.S. Pat. No. 7,988,725; expandable nail anchors as described herein; staple anchors as described by Morales U.S. Pat. No. 6,986,775.

Figure 21A:
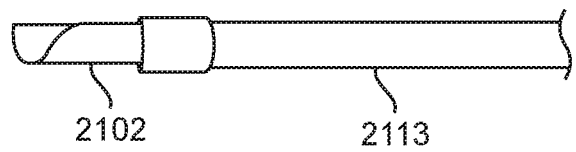
Figure 21B:
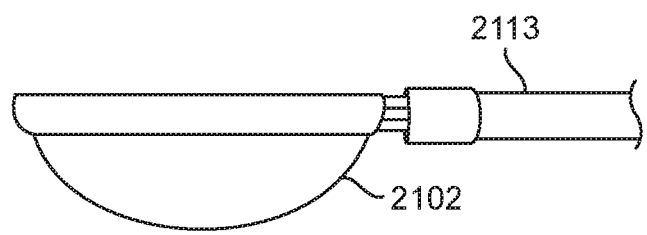
Figure 21C:
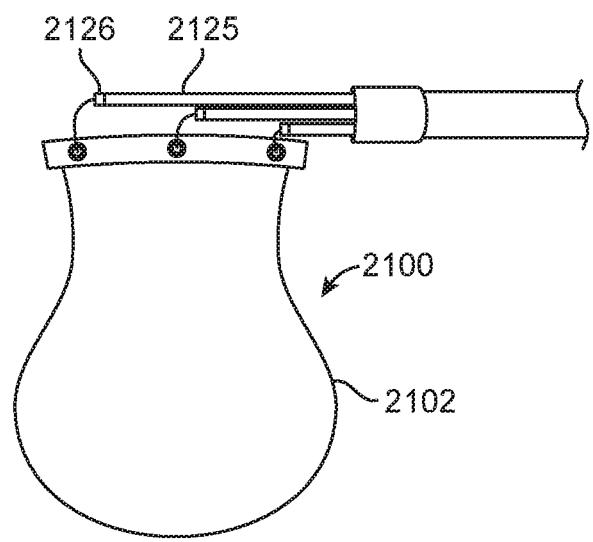
Figure 21D:
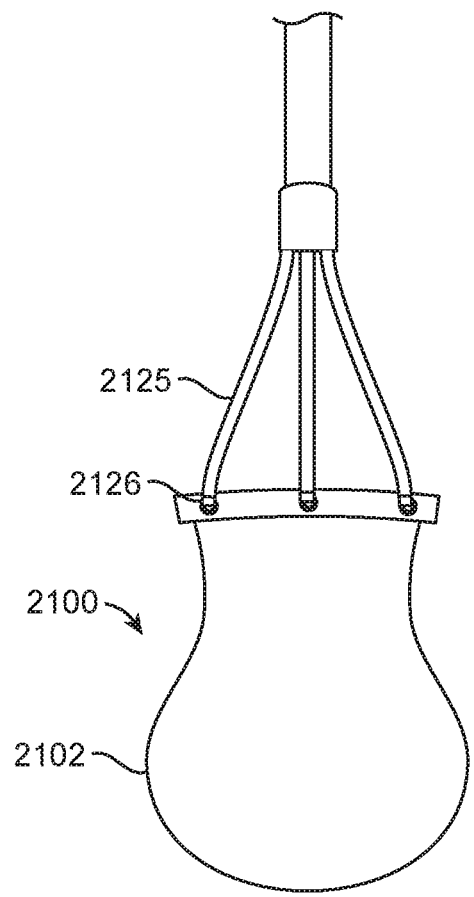

In an alternate embodiment, the coupling elements may be terminated in an anchoring mechanism, which is then used to affix the mitral assist device to the myocardium. FIG. 21 illustrates such a device. FIG. 21C is illustrated after the mitral assist device 2100 has been delivered from within the delivery catheter 2113, the device body has been unfurled, and the steerable coupling elements 2130 have been manipulated to a plane parallel to the longitudinal axis of the delivery catheter. During a deployment the device coupling locations would be aligned with or near the mitral annulus, and steered such that they were face-on to the myocardium. In such a configuration, the terminal anchoring mechanism may comprise any of the anchoring means previously described herein.

When the device body is comprised of a molded material as shown in FIG. 22, the perimeter stiffener 2230 may be molded in the device body 2202. In addition to a perimeter stiffener 2230, a flexural stiffener 2231 may be incorporated in the device body. Alternatively, a flexural stiffener may be comprised in along some longitudinal cross section of the device body. Such stiffeners in some embodiments will be sandwiched between a proximal and distal surface layer of a device body. Mitral assist device 2200 is comprised of device body 2202 and device strap 2211 with anchor elements 2238 deployed by anchor drive 2225. After helical anchoring screws 2239 are affixed into the myocardial tissue, guide sheath 2232 and guide lock 2233 are removed allowing the retrieval of anchor element drive 2225.

FIGS. 23A and 23B show a cross section of screw anchor system 2342 comprising screw anchor element 2334, screw anchor guide elements 2333 and 2332, and screw anchor drive 2335. FIG. 23A shows screw anchor drive 2335 positioned at, but not engaged with, anchor drive slot 2338, and FIG. 23B shows the drive element engaged with the drive slot. A guide system comprised of guide element lock 2333 and guide element sheath 2332 facilitate alignment and engagement of the drive to the drive slot. These guide elements run through screw drive anchor 2335 along a lumen traversing the length of the drive element and are removed from the assembly after deploying the anchoring element by removing guide lock 2333 which in turn releases guide sheath 2332 allowing the guide and drive elements to be removed from the anchoring element. FIGS. 23C and 23D illustrate the delivery and operational configurations of screw anchor element 2334 respectively, where helical screw element 2339 is deployed using screw anchor drive 2335 as described above in FIGS. 23A and 23B.

FIG. 24 represents one embodiment of a steerable delivery catheter for coupling elements. Steering is accomplished by a pulling on steering wire 2441 which causes catheter 2425 to bend. Alternate catheter steering systems known to the art may also be employed.

FIGS. 25 through 27 depict the delivery of a leaflet assist device as described herein using three different approaches. FIG. 25 shows a steerable delivery catheter delivering a device to a target area via an endovascular transseptal approach delivered from the inferior vena cava. As shown, the distal end of delivery catheter 2513 has been passed through the septum between the right and left atria. After which the mitral assist device was delivered from the delivery catheter and then oriented such that the mitral assist device body is positioned over the posterior mitral leaflet 2503 and between the anterior and posterior mitral leaflets. The device strap 2511 aligned with the annulus fibrous sinister at the perimeter of the posterior mitral leaflet 2504. The screw anchor system 2542 is then used to affix the mitral assist device in place. The delivery catheter 2513 as depicted in FIG. 25 is a steerable catheter as is known in the art. FIG. 26 depicts an endovascular arterial delivery approach, and FIG. 27 depicts a transapical approach.

FIG. 28 illustrates a mitral assist device in which a flexible stiffening element 2831 has been comprised in the perimeter of the mitral assist device body 2802 to minimize the upward displacement of the mitral assist device during mitral closure. The device body 2802 is comprised of a fabric, polymer sheet, or tissue, the stiffening mechanism may be sewn in place as shown. In some cases, a biasing material may be employed to cover the stiffening element. The stiffening element may be comprised of a polymer material, a super elastic material, or a combination of such materials.

Referring to FIG. 29, a leaflet assist or repair device 2900 may be used to assist or repair a failed prosthetic leaflet FPL. One such repair is illustrated in FIG. 29, where a percutaneously delivered prosthetic mitral valve PMV, delivered over the native mitral valve NMV, can be repaired by affixing the leaflet assist or repair device 2900 to the support structure of the prosthetic valve via a connector 2901. Such a connector 2901 may be chosen from any of those described herein, such as anchor or anchor elements 622, 722, 822, 922, 923, 1122, 1222, 1223, 1322, 1323, 2238, 2334, 2332, 2333, 2235, and 2542, to name a few. The leaflet assist or repair device 2900 may be similar to any of the prosthetic leaflet assist devices described herein, such as device 100. For instance, the leaflet assist or repair device 2900 may provide a surface to which a functional prosthetic leaflet may coapt.

Referring to FIG. 30, a leaflet assist or repair device 3000 may be used to assist or repair a failed natural leaflet via attachment of the leaflet assist or repair device 3000 to an annuloplasty ring APR previously placed in the heart. One such repair is illustrated in FIG. 30 where a percutaneously delivered annuloplasty ring APR has been used to improve the performance of a mitral valve MV. One leaflet of the mitral valve MV may be further supported by affixing the leaflet assist or repair device 3000 to the support annuloplasty ring APR via a connector 3001. Such a connector 3001 may be chosen from any of those described herein, such as anchor or anchor elements 622, 722, 822, 922, 923, 1122, 1222, 1223, 1322, 1323, 2238, 2334, 2332, 2333, 2235, and 2542, to name a few. The leaflet assist or repair device 3000 may be similar to any of the prosthetic leaflet assist devices described herein, such as device 100. For instance, the leaflet assist or repair device 3000 may provide a surface to which a functional natural leaflet may coapt.

FIGS. 29 and 30 additionally show various native anatomical features of the heart, such as the right atrium RA, the left atrium LA, the pulmonic valve PV, the tricuspid valve TV, the mitral valve MV, the chordae tendineae CT, the right ventricle RV, the left ventricle LV, and the septum ST.

Figure 31A:
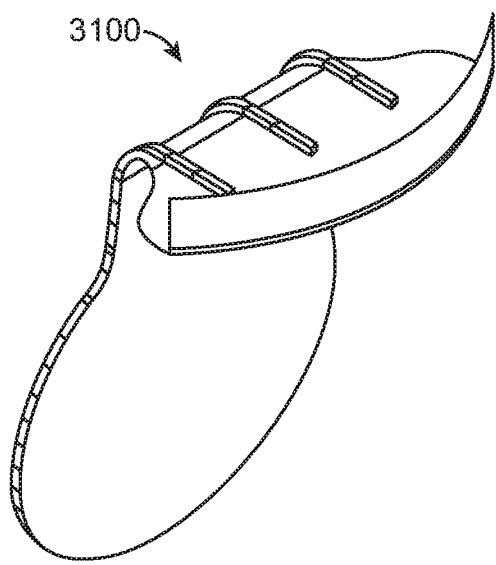
Figure 31B:
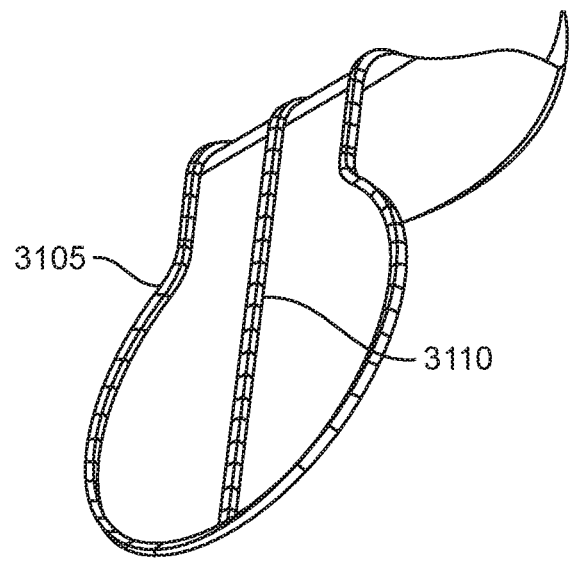
Figure 31C:
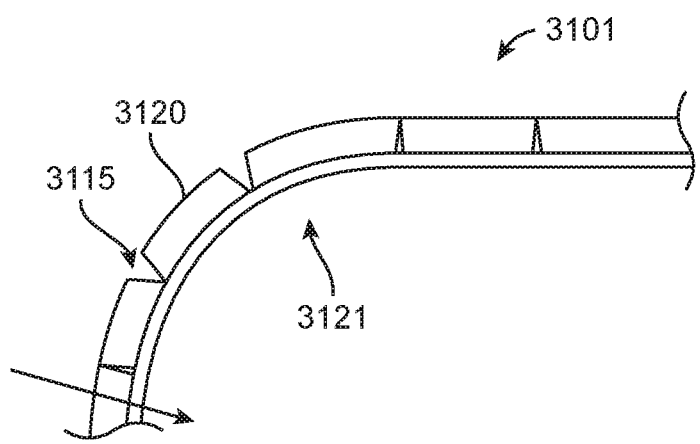
Figure 31D:
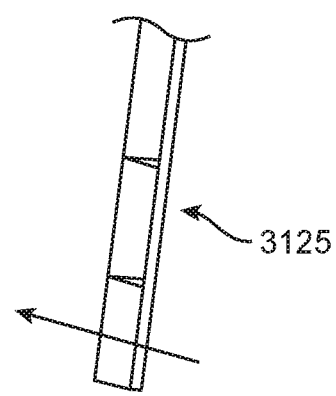

FIGS. 31A through 31D illustrate features of a leaflet assist device 3100 which may comprise directionally sensitive stiffeners, two directionally sensitive edge stiffeners 3105 and one directionally sensitive central stiffener 3110. The stiffeners 3105, 3110 may be similar to those described herein above with the exception that the directionally sensitive stiffeners 3105, 3110 may be comprised of multiple slices or spaces 3115 between multiple raised sections 3120 such that when bent in a compliant direction 3121 (such as when a force is applied in a direction indicated by arrow 3103) as shown in FIG. 31C, the spaces or slices 3120 can open and cause the device to have a curved section 3101, and therefore the stiffness is that provided by the membrane portion of the leaflet of the device. In contrast, when the leaflet is bent in a stiff direction 3125 (such as when a force is applied in a direction indicated by arrow 3123) the spaces close and the raised sections provide additional stiffness as shown in FIG. 31D.

FIGS. 32A and 32B illustrate a leaflet assist device 3200 attached to the mitral valve annulus MVA of a mitral valve MV which has been repaired with a leaflet fixation device such as a mitral clip MC (as shown in FIGS. 32A, 32B) or suture. In some case, when a mitral clip MC, or such a device, is used, the improvement in coaptation and therefore reduction in regurgitation may not be sufficient and/or over time, the improvement resulting from the use of the mitral clip MC may be reduced. In such cases, a leaflet assist device 3200 may be used in conjunction with the mitral clip MC. In the configuration illustrated, the leaflet assist device 3200 may be mounted perpendicular to the axis of the coaptation of the leaflets by connectors 3201. FIG. 32A illustrates the vale MV in diastole when the leaflet assist device is folded downwards, allowing blood flow through the valve MV. FIG. 32B illustrates the mitral valve MV in systole where the leaflet assist device 3200 has been pushed up and can provides shelf to stop the native leaflets from moving further up, thereby enhancing coaptation.

FIGS. 33A and 33B illustrate another embodiment for a leaflet assist device 3300 for use in a native mitral valve MV previously treated with a leaflet fixation device, in this case, a mitral clip MC, where the leaflet assist device 3300 is configured to be attached to the mitral valve annulus MVA parallel to the axis of coaptation. As shown, the coaptation device 3300 may comprise two leaflets 3301 such that one leaflet is on each side of the leaflet fixation device. In some embodiments, the leaflet assist device 3300 comprises only one leaflet 3301 for treating one half of the coaptation. FIG. 33A illustrates the valve MV in diastole and FIG. 33B illustrates the valve MV in systole.

FIG. 34 illustrates an embodiment of leaflet assist device 3400 similar to that illustrated in 33B which comprises a directionally sensitive center stiffener 3403 and two leaflets—a first leaflet 3401a and a second leaflet 3401b. The directionally sensitive center stiffener 3403 may be similar to the other directionally sensitive stiffeners described herein and vice versa (e.g., it may have a plurality of slices or spaces on one side to facilitate bending in one direction and resist bending in the other, opposite direction.)

FIG. 35 illustrates a cross section of a mitral valve with a semi-flexible leaflet assist device 3500 placed over the posterior mitral leaflet (PML) such that it coapts with the anterior mitral leaflet (AML). The leaflet assist device 3500 is anchored along the annulus of the mitral valve and can be anchored by any of the methods described elsewhere herein. The dashed line 3501 represents the level of the upper most natural and or desired flexure the native leaflets when the valve is closed, herein described as flexural level. In the mitral valve, this level will be at or near the most atrial level of the annulus.

Such a leaflet assist devices may be comprised of pericardia, artificial tissue or other synthetic material (i.e., Dacron). The leaflet assist device 3500 comprises a stiffer periphery 3530. The periphery 3530 may be stiffened by stitching applied to the edge. In some embodiments, a stiffener may be comprised in the stitching applied to the edge, such as a nitinol wire. In some embodiments, the leaflet assist device 3500 may be comprised of two layers and the stitching around the periphery 3530 used to attach the two layers. FIG. 36 illustrates such a leaflet 3600 comprised of two layers of pericardia sewn together at a stiffened periphery 3630.

FIGS. 37 through 40 illustrate embodiments of leaflet assist devices which enhance coaptation (as shown by coaptation area CA) by placing a patch or barrier at or near the flexural level of the mitral valve. Typically, these devices will be placed such that they limit the natural leaflet movement to level at or less than the flexural level. Such devices may be used in combination with or independently of the device of FIG. 36 or other leaflet assist devices described herein. Such devices may be attached screws, stapes, sutures, or any other suitable means including any previously described herein.

Figure 37:
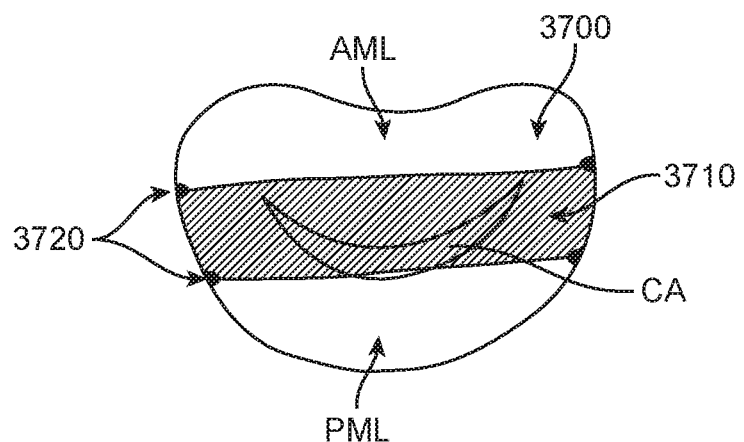

FIG. 37 illustrates a leaflet assist device 3700 comprised of a rectangular sheet 3710 placed just below the flexural level of a mitral valve. Such a device will limit the movement of the native, and or other mitral assist device, to the level of its placement. As illustrated, the leaflet assist device 3700 attachments 3720 are at the 4 corners. This will enhance coaptation of the valve by forcing better coaptation and covering areas of poor coaptation.

Figure 38:
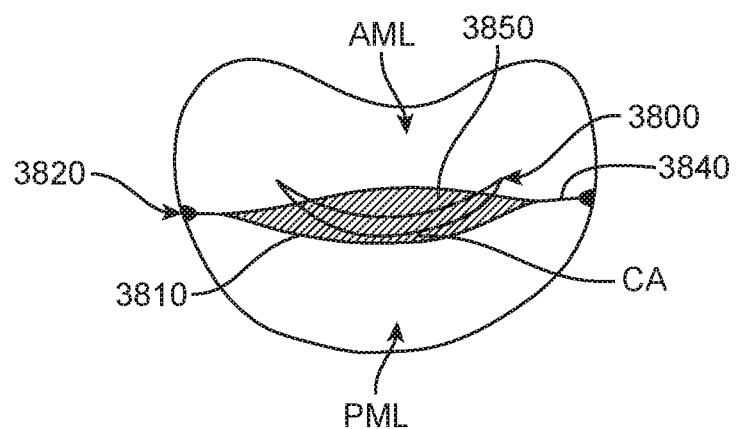
Figure 39:
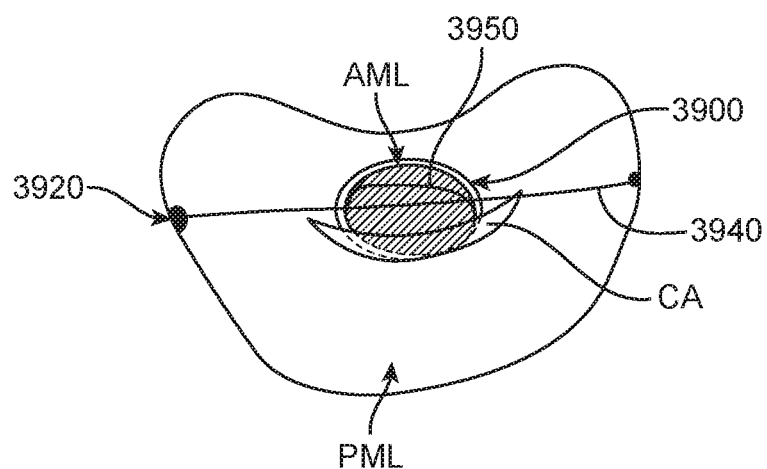

The embodiments of FIG. 38 and FIG. 39 illustrate alternative coaptation devices 3800 and 3900, respectively, comprising volume filling components. The volume filling components as illustrated here are a spindle bead 3850 in FIG. 38 and a spherical shaped bead 3950 in FIG. 39. Such volume filling components are anchored on tethers 3840 and 3940 by means as described elsewhere herein. In some embodiments, the volume filling components are elastomeric balloons which are inflated in situ, in other embodiments they may be self-swelling. The coaptation device 3800 may further comprise sheets 3810 and attachments 3820 as in the device 3700 described in FIG. 37. The coaptation device 3900 may further comprise attachments 3920 as in the device 3700 described in FIG. 37.

Figure 40:
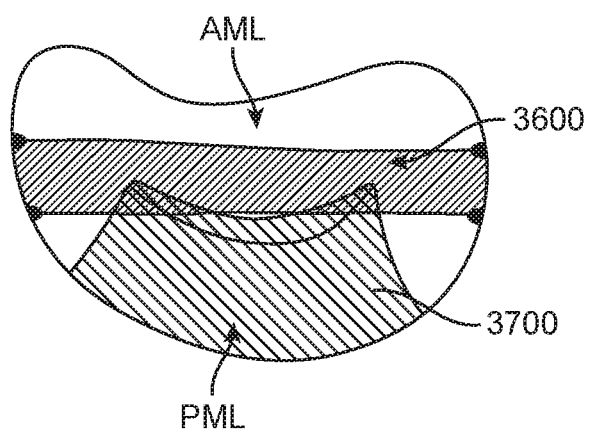

FIG. 40 illustrates an embodiment in which a leaflet 3600 such as that described in FIG. 36 is used in combination with a leaflet assist device 3700 such as that described in FIG. 37.

Although the leaflet assist devices described herein are generally described in the context of the mitral valve, they can be used to enhance the performance of any of the in the circulatory system.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method comprising:
advancing, to within a heart, a leaflet assist device comprising two prosthetic leaflets; and
attaching the leaflet assist device to a native valve annulus of a native cardiac or venous valve of the heart or to an annuloplasty ring previously placed in the heart, so that the two prosthetic leaflets are adjacent each other and lie over a superior surface of (a) a first native valve leaflet of the native cardiac or venous valve or (b) a first defective prosthetic leaflet coupled to the annuloplasty ring at a first side of the native valve annulus, leaving at least (a) a second native valve leaflet of the native cardiac or venous valve or (b) a second prosthetic leaflet coupled to the annuloplasty ring at a second side of the native valve annulus uncovered by any prosthetic leaflet of the leaflet assist device,
wherein the attaching of the leaflet assist device to the native valve annulus or the annuloplasty ring comprises attaching, to the native valve annulus or the annuloplasty ring, an anchor coupled to the two prosthetic leaflets of the leaflet assist device, such that the anchor fully or partially circumscribes the native valve annulus or the annuloplasty ring, and
wherein the two prosthetic leaflets of the leaflet assist device comprise respective fixed ends and free ventricular ends, the fixed ends being sealingly and continuously coupled to the anchor along respective entire lengths of the fixed ends.

2. The method according to claim 1, wherein the attaching of the leaflet assist device to the native valve annulus or to the annuloplasty ring comprises attaching the leaflet assist device to a mitral valve.

3. The method according to claim 1, wherein the attaching comprises attaching the leaflet assist device to the native cardiac or venous valve, the native cardiac or venous valve previously treated with a leaflet fixation device.

4. The method according to claim 1, wherein each prosthetic leaflet of the leaflet assist device is sufficiently flexible so that the free ventricular end is freely moveable and will move in unison with (a) the first native valve leaflet of the native cardiac or venous valve or (b) the first defective prosthetic leaflet coupled to the annuloplasty ring to coapt with (a) the second native valve leaflet or (b) the second prosthetic leaflet coupled to the annuloplasty ring in response to blood flow through the native cardiac or venous valve.

5. The method according to claim 1, wherein at least one of the two prosthetic leaflets of the leaflet assist device comprises a body formed from tissue or a synthetic polymer.

6. The method according to claim 1, wherein at least one of the two leaflets of the leaflet assist device comprises a stiffening element.

7. The method according to claim 6, wherein the stiffening element is directionally sensitive.

8. The method according to claim 6, wherein the stiffening element comprises a plurality of slices or spaces between multiple raised sections.

9. The method according to claim 6, wherein the stiffening element is provided at an inner side of each of the two prosthetic leaflets of the leaflet assist device.

10. The method according to claim 1,
wherein the attaching of the leaflet assist device to the native valve annulus or to the annuloplasty ring comprises attaching the leaflet assist device to a mitral valve, and
wherein the attaching of the leaflet assist device to the native valve annulus or to the annuloplasty ring further comprises placing a barrier of the leaflet assist device at or near a flexural level of the mitral valve, such that the barrier limits a movement of the first native valve leaflet or the first defective a leaflet to a level at or less that the flexural level.

11. The method according to claim 10, wherein the placing of the barrier comprises placing a rectangular sheet of the barrier below the flexural level of the mitral valve.

12. The method according to claim 1, wherein the respective free ventricular ends of the prosthetic leaflets of the leaflet assist device are spaced apart from each other such that the two prosthetic leaflets of the leaflet assist device do not coapt with each other when coapting with (a) the second native valve leaflet of the native cardiac or venous valve or (b) the second prosthetic leaflet coupled to the annuloplasty ring.

13. The method according to claim 1, wherein the second side of the native valve annulus is located opposite to the first side of the native valve annulus.

14. The method according to claim 1, wherein the attaching of the leaflet assist device to the native valve annulus or to the annuloplasty ring comprises attaching the leaflet assist device to an aortic valve.

15. The method according to claim 1, wherein the attaching of the leaflet assist device to the native valve annulus or to the annuloplasty ring comprises attaching the leaflet assist device to a tricuspid valve.

16. The method according to claim 1, wherein the native cardiac or venous valve of the heart further comprises a third native valve leaflet, and wherein the attaching of the leaflet assist device to the native valve annulus or the venous valve of the heart leaves both the second native valve leaflet and the third native valve leaflet uncovered by any prosthetic leaflet of the leaflet assist device.

17. The method according to claim 1, wherein a third prosthetic valve leaflet is coupled to the annuloplasty ring at a third side of the native valve annulus, and wherein the attaching of the leaflet assist device to the annuloplasty ring leaves both the first prosthetic valve leaflet coupled to the annuloplasty ring and the second prosthetic valve leaflet coupled to the annuloplasty ring uncovered by any prosthetic leaflet of the leaflet assist device.

18. The method according to claim 1, wherein the fixed ends of the two prosthetic leaflets of the leaflet assist device are contiguous.

19. The method according to claim 1, wherein the two prosthetic leaflets of the leaflet assist device are continuous.

20. The method according to claim 1, wherein the two prosthetic leaflets of the leaflet assist device are comprised of a single fabric, polymer sheet, or tissue.

* * * * *